US009816129B2

(12) United States Patent
Kelley et al.

(10) Patent No.: US 9,816,129 B2
(45) Date of Patent: *Nov. 14, 2017

(54) BIOPROBES AND METHODS OF USE THEREOF

(71) Applicant: The Governing Council of the University of Toronto, Toronto (CA)

(72) Inventors: Shana O. Kelley, Toronto (CA); Zhichao Fang, Toronto (CA); Elizaveta Vasilyeva, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/091,369

(22) Filed: Apr. 5, 2016

(65) Prior Publication Data

US 2016/0298177 A1 Oct. 13, 2016

Related U.S. Application Data

(63) Continuation of application No. 13/983,934, filed as application No. PCT/US2012/024015 on Feb. 6, 2012, now Pat. No. 9,335,289.

(60) Provisional application No. 61/440,336, filed on Feb. 7, 2011.

(51) Int. Cl.
*C12Q 1/68* (2006.01)
*G01N 27/26* (2006.01)
*G01N 27/327* (2006.01)

(52) U.S. Cl.
CPC ......... *C12Q 1/6816* (2013.01); *C12Q 1/6837* (2013.01); *C12Q 1/6886* (2013.01); *G01N 27/26* (2013.01); *G01N 27/3276* (2013.01); *G01N 27/3277* (2013.01); *C12N 2310/3181* (2013.01)

(58) Field of Classification Search
None
See application file for complete search history.

(56) References Cited

U.S. PATENT DOCUMENTS

| | | | |
|---|---|---|---|
| 7,361,470 B2 | 4/2008 | Kelley et al. | |
| 7,741,033 B2 | 6/2010 | Kelley et al. | |
| 9,335,289 B2 * | 5/2016 | Kelley | C12Q 1/6816 |
| 2005/0084881 A1 | 4/2005 | Kelley et al. | |
| 2005/0239121 A1 | 10/2005 | Gall et al. | |
| 2007/0082351 A1 | 4/2007 | Stender et al. | |
| 2011/0233075 A1 | 9/2011 | Soleymani et al. | |

FOREIGN PATENT DOCUMENTS

WO  WO-2010025547  3/2010

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Egholm et al., "Peptide nucleic acids (PNA). Oligonucleotide analogs with an achiral peptide backbone," Journal of American Chemical Society, 114(5):1895-1897 (1992).
European Search Report EP 12744938.7, dated Sep. 12, 2014 (8 pages).
Fang et al., "Direct electrocatalytic mRNA detection using PNA-nanowire sensors," Analytical Chemistry, 81(2):612-617 (2009).
PCT International Search Report and Written Opinion of the International Searching Authority of Application No. PCT/US2012/024015, dated Jul. 13, 2012 (16 pages).
Silvester et al., "Effect of terminal amino acids on the stability and specificity of PNA-DNA hybridisation," Organic and Biomolecular Chemistry, 5(6):917-923 (2007).
Yang et al.,"Direct, electronic microRNA detection for the rapid determination of differential expression profiles," Angewandte Chemie International Edition, 48(45):8461-8464 (2009).

* cited by examiner

Primary Examiner — James Martinell

(57) ABSTRACT

Disclosed are biomolecule based bioprobes that exhibit improved water solubility and mono layer-forming properties with substantially little or no aggregation that can appreciably interfere with binding of the bioprobes to a target nucleotide. The bioprobes may be used in conjunction with a suitable reporter system to detect very small quantities of biological markers. The bio-probes comprise a nucleobase sequence capable of hybridizing to a target nucleotide; and at least one charged functional group attached to said nucleobase sequence. Also disclosed are biosensors, and sensing devices that comprise the bin-probe. Further disclosed are suitable electrochemical reporter systems for use with the bioprobes. Methods of use of these devices and probes, including for the detection of target biomarkers, including biomarkers for cancer cells or pathogens, are also included.

17 Claims, 8 Drawing Sheets

FIG. 2A
*bcr | abl*
CAGAGTTCAA | AAGCCCTTCA
(SEQ ID NO: 15)
FIG. 2B
DNA probe
PNA probe
ANA probe
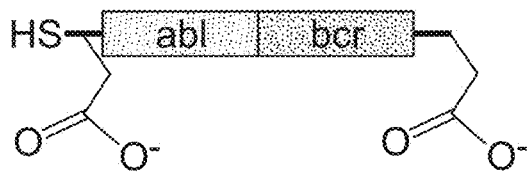
FIG. 2C
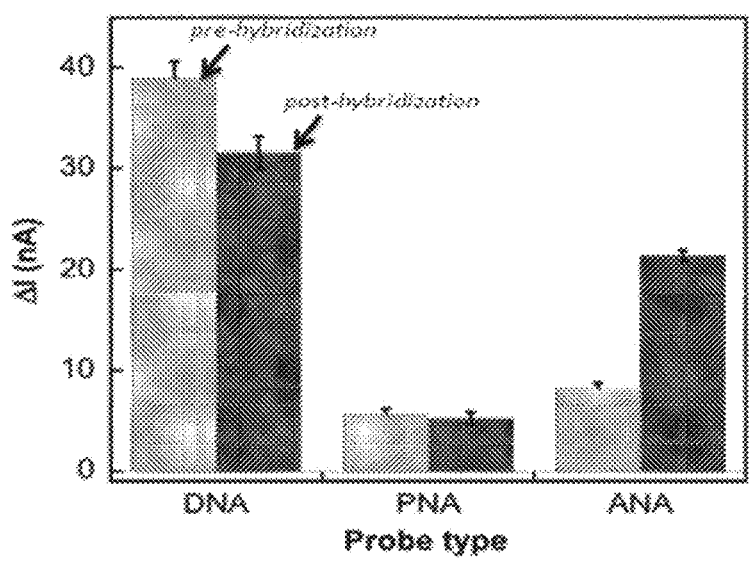

SEQUENCE LISTING

```
<160> NUMBER OF SEQ ID NOS: 18

<210> SEQ ID NO 1
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gly
1

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any charged amino acid

<400> SEQUENCE: 2

Cys Gly Xaa
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any charged amino acid
```

```
<400> SEQUENCE: 3

Cys Gly Xaa Xaa
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any charged amino acid

<400> SEQUENCE: 4

Cys Gly Xaa Xaa Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any charged amino acid

<400> SEQUENCE: 5

Cys Gly Xaa Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Any charged amino acid

<400> SEQUENCE: 6

Cys Gly Xaa Xaa Xaa
1               5

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any charged amino acid

<400> SEQUENCE: 7

Cys Gly Xaa
1

<210> SEQ ID NO 8
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any charged amino acid

<400> SEQUENCE: 8

Cys Gly Xaa
1

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any charged amino acid

<400> SEQUENCE: 9

Cys Gly Xaa
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any charged amino acid

<400> SEQUENCE: 10

Cys Gly Xaa Xaa
1

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tgaagggctt cttccttatt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tgaagggctt ttgaactctg                                              20
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tgaagggctt ttgaactctg                                             20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
atctgctctg tggtgtagtt                                             20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cagagttcaa aagcccttca                                             20

<210> SEQ ID NO 16
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any charged amino acid

<400> SEQUENCE: 16

Xaa
1

<210> SEQ ID NO 17
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any charged amino acid

<400> SEQUENCE: 17

Xaa Xaa
1

<210> SEQ ID NO 18
<211> LENGTH: 3
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any charged amino acid

<400> SEQUENCE: 18

Xaa Xaa Xaa
1
```

BIOPROBES AND METHODS OF USE THEREOF

CROSS-REFERENCE TO RELATED APPLICATIONS

This application is a continuation of U.S. patent application Ser. No. 13/983,934, which is a United States National Stage Application filing under 35 U.S.C. §371 of International Application No. PCT/US2012/024015, filed on Feb. 6, 2012, which claims the benefit of priority of U.S. Provisional Patent Application Ser. No. 61/440,336, filed Feb. 7, 2011, both of which are hereby incorporated by reference herein in their entireties.

SEQUENCE LISTING

The instant application contains a Sequence Listing which has been submitted electronically in ASCII format and is hereby incorporated by reference in its entirety. Said ASCII copy, created on Apr. 4, 2016, is named 109904-0006-302_SL.txt and is 4,827 bytes in size.

TECHNICAL FIELD

The present disclosure relates generally to biosensors, biosensor arrays, probes for biosensors and a method for detecting biomarkers using a biosensor. The disclosure also relates to biomolecule based bioprobes that have reduced or are free of aggregation. The biomolecule-based bioprobes may further be used in conjunction with an electrochemical reporter system to detect small quantities of biological markers.

BACKGROUND OF THE INVENTION

Detection and analysis of low concentrations of analytes in various biologic and organic environments is becoming increasingly important. For a sensing approach to be useful not only for diagnosis, but also to monitor low levels of residual disease, the limits of detection must presently reach low levels, for example femtomolar levels, to achieve the detection of scarce analytes in clinical samples with an acceptably low level of false negatives. High levels of specificity are required to ensure low levels of false positives. From a practical perspective, equally important is a streamlined approach to sample workup, since the need for extensive sample processing can overwhelm the benefits of a sensor's innate high sensitivity and specificity.

Qualitative analysis is generally limited to the higher concentration levels, whereas quantitative analysis usually requires labeling with a radioisotope or fluorescent reagent. Such procedures are generally time consuming and inconvenient. Recent advances in developing bioelectronic biological marker analysis systems open up new opportunities for molecular diagnostics and have attracted substantial research efforts (Boon, E. M., et al., *Nat. Biotechnol.*, 18, 1096, 2000; Rodriguez, M. & Bard, A., *J. Anal. Chem.*, 62, 1658, 1990). Optical (Jordan, C. E., et al., *Anal. Chem.*, 69, 4939, 1997; Fotin, A. V., et al., *Nucleic Acids Res.*, 26, 1515, 1998), electrochemical (Kelley, S. O., et al, *Bioconjug. Chem.*, 8, 31, 1997; Kelly, S. O., et al., *Nucleic Acids Res.*, 27, 4830, 1999), and microgravimetric and quartz-crystal microbalance (Bardea, A., 30 et al., *Chem. Commun.*, 839, 1998; Wang, J., *Nucleic Acids Res.*, 28, 3011, 2000), transduction methods have been reported for the detection of DNA hybridization events.

One of the objectives disclosed herein is to provide biomolecule based bioprobes that are free of aggregation. Another object is the use of the disclosed bioprobes useful to detect small quantities of biological markers. Another objective is to provide biosensors that comprise the bioprobes described herein. An additional objective is to provide biosensors that comprise the bioprobes described herein, immobilized on a suitable substrate, and a suitable reporter system attached thereto.

SUMMARY OF THE INVENTION

Disclosed are methods and systems for the detection and manipulation of biomolecules using biomolecule based bioprobes described herein.

This disclosure relates to a new class of bioprobe molecules based on amino acid/nucleic acid chimeras that increase sensitivity and selectivity, and overcome limitations that may arise when using probe molecules, including poor solubility, aggregation, and poor monolayer quality. Also provided are biosensors, comprising the bioprobes described herein. Disclosed herein are biosensors that require only a single, simple cell lysis step prior to analysis. In some embodiments, the samples tested using the biosensors disclosed herein are substantially unpurified.

In one embodiment, disclosed herein are bioprobes that comprise a nucleobase sequence capable of hybridizing to a target nucleotide; and at least one charged functional group comprising an anionic functional group, a cationic functional group and/or a charged amino acid attached to the nucleobase sequence. In certain embodiments, the nucleobase sequence is a nucleic acid sequence such as ribonucleic acid (RNA), deoxyribonucleic acid (DNA) or analog 20 thereof, including, for example, a morpholino nucleic acid, a methyl phosphonate nucleic acid and a peptide nucleic acid (PNA), which contains a backbone comprised of N-(2-aminoethyl)-glycine units linked by peptides rather than deoxyribose or ribose, peptide nucleic acids, locked nucleic acids, or phosphorodiamidate morpholino oligomers. Under appropriate conditions, the probe can hybridize to a complementary nucleic acid to provide an indication of the presence of the complementary nucleic acid in the sample.

In certain embodiments, the anionic functional group is a carboxylate, a sulfate or a sulfonate. In certain embodiments, the cationic functional group is an amine or guanadinum group. In some embodiments, the charged amino acid is an L-amino acid comprising a net positive charge such as Lysine (Lys, K), Ornithine (Orn, O), Diamino-butyric acid (Dab), Diamino-propionic acid (Dap), and Arginine (Arg, R). In some embodiments, the charged amino acid is an L-amino acid or a D-amino acid comprising a net negative charge such as Aspartic acid (Asp, D), Glutamic acid (Glu, E), or Aminoadipic acid (Aad), 4-phosphonomethyl-L-phenylalanine, 4-phosphonomethyl-D-phenylalanine, L-carboxyglutamic acid, D-carboxyglutamic acid, 5-Amino Salicylic Acid or any other charged amino acid from the group shown in Table 2.

In certain embodiments, the probe also comprises a peptide or a protein that is able to bind to or otherwise interact with a biomarker target (e.g. receptor or ligand) to provide an 5 indication of the presence of the ligand or receptor in the sample. The probe may include a functional group (e.g., thiol, dithiol, amine, carboxylic acid) that facilitates binding with an electrode. Probes may also contain other features, such as longitudinal spacers, double-stranded and/or single-stranded regions, polyT linkers, double stranded duplexes as rigid linkers and PEG spacers. Bioprobes can be immobilized on resins, nanoparticles, nanocrystals, or microparticles.

In some embodiments, the bioprobe is associated with an electrode. In certain embodiments, the electrode is a microelectrode. In some embodiments, the microelectrode is a nanostructured microelectrode (NME). In further embodiments, the electrodes are present as a plurality of electrodes arrayed on a substrate.

In certain embodiments the bioprobe associated electrodes may be prepared on a biosensing device, such as a chip-based format, such that a series of electrodes may be made on a single chip to enable multiplexed experiments.

In certain embodiments are provided biosensing devices, such as integrated circuits, comprising, for example, a substrate; an electrically conductive lead on the substrate; an insulating or passivation layer covering the lead, the insulating layer having an aperture exposing a portion of the lead; and an electrode in electrical communication with the exposed portion of the lead, the electrode being adapted to generate a charge in response to a biomolecular stimulus such as hybridization or interaction.

In some embodiments are methods for carrying out a biosensing process using electrodes containing a bioprobe incorporated into a device; biasing the microelectrode relative to a reference electrode; measuring a reference charge or reference current flow between the microelectrode and the reference electrode; exposing the electrode containing the bioprobe to a biomolecular stimulus (e.g., hybridization with a complementary nucleic acid or binding with a binding partner present in a biological sample); measuring a charge or current flow generated at the microelectrode in response to the biomolecular stimulus; and determining the amount of biomolecular stimulus present by comparing the measured charge or measured current flow against the reference charge or reference current flow.

In certain embodiments are methods of detecting a biomolecule or a biomarker, using the bioprobes and biosensing devices described herein. The method involves contacting a purified or unpurified sample with a biosensing device that comprises a bio-probe comprising a nucleobase sequence capable of hybridizing to the target biomarker of interest, and at least one charged functional group attached to said nucleobase sequence; hybridizing the bio-probe to the target biomarker; and detecting the hybridization as being indicative of presence of the biomarker of interest in the sample. In certain embodiments, this detection is performed by means of a redox-active reporter. In certain embodiments, this method is used to detect the presence of target biomolecules in solutions, such as biological fluids obtained from a test subject.

In some embodiments, provided are methods of identification of a specific biomolecule (e.g., nucleic acids) within a population of heterogeneous biomolecules. The method comprises contacting a bio-probe comprising a nucleobase sequence capable of hybridizing to the target biomolecule of interest, and at least one charged functional group attached to said nucleobase sequence; hybridizing the bio-probe to the target biomolecule; and detecting the hybridization as being indicative of presence of the biomolecule of interest.

In certain embodiments are methods of diagnosing a disease or condition in a subject, using the bioprobes and biosensing devices described supra. In certain embodiments, the disease is a cancer. In certain embodiments is a method of detecting the presence of cancer cells in a biological sample, comprising: contacting the sample with a bio-probe comprising a nucleobase sequence capable of hybridizing to a target biomarker, and at least one charged functional group attached to said nucleobase sequence; hybridizing the bioprobe to the target gene sequence; and detecting the hybridization as being indicative of the presence of cancer cells in the sample.

In some embodiments, the cancer being diagnosed or detected is selected from the group consisting of breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, melanoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas. In other embodiments, the cancer being treated is pancreatic cancer, liver cancer, breast cancer, osteosarcoma, lung cancer, soft tissue sarcoma, cancer of the larynx, melanoma, ovarian cancer, brain cancer, Ewing's sarcoma or colon cancer.

In yet another embodiment, a method for conducting a business, including providing biosensors disclosed herein to a physician or health care provider, is provided.

In other embodiments, the sample is obtained from a subject which is a mammal, preferably a human. In some embodiments, the sample may include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors or organs.

These and other aspects, embodiments, objects and features disclosed herein will be more fully appreciated when the following detailed description is read in conjunction with the accompanying drawings.

BRIEF DESCRIPTION OF THE DRAWINGS

FIG. 1A shows the layout of the chip wherein a gold pattern is deposited on the chip surface with 8 external contacts that are extended to narrow leads of a terminal width of microns. A passivating layer of silicon dioxide is applied to the chip, and then 5 micron apertures are opened at the end of each lead to provide a microelectrode template.

FIG. 1B is a scanning electron micrograph of a 100 micron sensor formed using gold electrodeposition on the surface of the chip.

FIG. 1C shows sequence of steps used for nucleic acids analysis. The sensors are first functionalized with probe molecules, and then hybridized with a target-containing solution.

FIG. 1D shows Ru(III)/Fe(III) reporter groups then permits hybridized material to be detected.

FIG. 1E depicts the overall flow of analysis trial.

FIGS. 2A-2D show the target and the bioprobes.

FIG. 2A depicts the junction region between the bcr gene and the abl gene within the mRNA expressed that generates the bcr-abl kinase.

FIG. 2B shows structures of DNA, PNA, and ANA (amino-acid/nucleic acids chimera) bioprobes.

FIG. 2C shows testing of DNA, PNA and ANA probes for hybridization of mRNA isolated from the K562 cell line that carries the bcr-abl gene fusion FIG. 2D shows different placement options for charged amino acids in conjugation with a 20 nucleobase probe sequence to generate bioprobes described here.

FIG. 4A shows K562 lysates wherein signals obtained before and after incubation of probe-modified microelectrodes with lysates of K562 cells were compared by monitoring the limiting reductive current in a Ru(III)/Fe(III) electrocatalysis solution. Total volume of samples was 30 microliters.

FIGS. 4B and 4C are representative differential pulse voltammograms showing the change in signal when lysates containing 10 and 1000 cells were introduced. Dotted lines represent the signal collected before hybridization, and the solid lines are signals collected after hybridization.

FIG. 4D shows detection of the bcr-abl gene fusion in CML patient leukocytes. Lysates were generated from 10-1000 cells, and signal changes monitored after 30 minutes. The presence of the bcr-abl fusion was confirmed using PCR (inset). Primers specific to each gene were used to analyze a fragment of the fusion, and used with K562 cells (left band) and patient cells (right band).

FIG. 4E shows detection of the bcr-abl gene fusion in whole blood.

DETAILED DESCRIPTION OF THE INVENTION

Figure 1A:
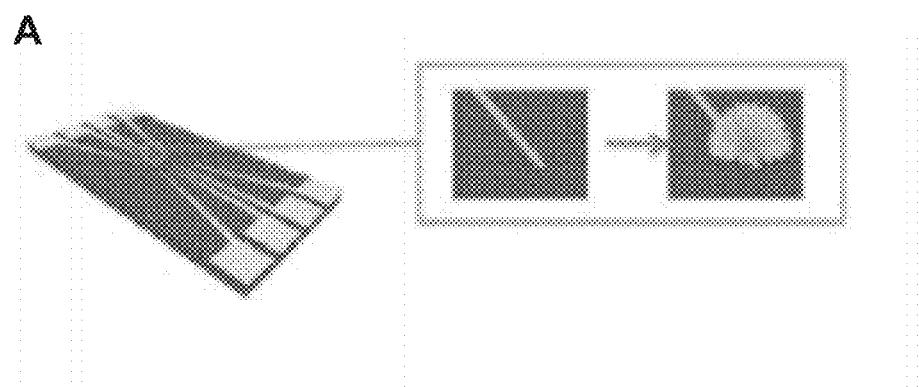
FIGS. 1A-1E depict chip-based biosensors.

In one embodiment, disclosed herein are bioprobes that comprise a nucleobase sequence capable of hybridizing to a target nucleotide; and at least one charged functional group comprising at least one anionic functional group, cationic functional group and/or a charged amino acid attached to the nucleobase sequence. In some embodiments, the nucleobase sequence is a nucleic acid sequence such as ribonucleic acid (RNA), deoxyribonucleic acid (DNA) or analog thereof, including, for example, a peptide nucleic acid (PNA), which contains a backbone comprised of N-(2-aminoethyl)-glycine units linked by peptides rather than deoxyribose or ribose, peptide nucleic acids, locked nucleic acids, or phosphorodiamidate morpholino oligomers. Under appropriate conditions, the probe can hybridize to a complementary nucleic acid to provide an indication of the presence of the nucleic acid in the sample.

In certain embodiments, the anionic functional group is a carboxylate, sulfate or sulfonate. In certain embodiments, the cationic functional group is an amine or guanadinum group. In certain embodiments, the charged amino acid is a chiral amino acid, which is an L-amino acid or a D-amino acid. In certain embodiments, the amino acid comprises a net positive charge such as Lysine (Lys, K), Ornithine (Orn, O), Diamino-butyric acid (Dab), Diamino-propionic acid (Dap), and Arginine (Arg, R). In certain embodiments, the charged amino acid comprises a net negative charge such as Aspartic acid (Asp, D), Glutamic acid (Glu, E), Aminoadipic acid (Aad), 4-phosphonomethyl-L-phenylalanine, 4-phosphonomethyl-D-phenylalanine, L-carboxyglutamic acid, D-carboxyglutamic acid, 5-Amino Salicylic Acid or any other charged amino acid selected from the group shown in Table 2.

In one embodiment, disclosed herein is a bio-probe, comprising:

a nucleobase sequence capable of hybridizing to a target nucleotide;

at least one charged functional group attached to said nucleobase sequence, wherein said charged functional group comprises a cationic functional group, an anionic functional group, a charged amino acid, or a combination thereof; and wherein attachment of said charged functional group to said nucleobase results in lesser aggregation of a plurality of bio-probes, as compared to bio-probes not comprising a charged functional group attached to said nucleobase.

In one embodiment, the bioprobes do not aggregate with a plurality of bio-probes. In another embodiment, the nucleobase sequence is a DNA, RNA, PNA, morpholino nucleic acid, or methyl phosphonate nucleic acid oligomer. In yet another embodiment, the nucleobase sequence is a PNA. In another embodiment, the anionic functional group is a carboxylate, a sulfate or a sulfonate. In still another embodiment, the cationic functional group is an amine or a guanadinum. In other embodiments, the amino acid is Asp, Glu, Aad, Ser, Lys, Orn, Dab, Dap, Arg, 4-phosphonomethyl-L-phenylalanine, 4-phosphonomethyl-D-phenylalanine, L-carboxyglutamic acid, D-carboxyglutamic acid, 5-Amino Salicylic Acid, or an amino acid shown 30 in Table 2.

In some embodiments, the bio-probe comprises between about 10 and about 40 nucleobases. In other embodiments, the bio-probe comprises between about 1 and about 20 charged functional groups. In still other embodiments, the charged functional groups are arranged as shown in Table 3. In some embodiments, the bio-probes are immobilized to a surface, wherein the surface may be nitrocellulose, nylon membrane, glass plate, or a polyvinyldifluoride surface. In some embodiments, the surface may be a multi-well plate, a resin, a nanoparticle, a nanocrystal, or a microparticle. In other embodiments, the bioprobe is immobilized to an electrode. In still other embodiments, the bio-probe further comprises a redox 5 label, wherein the bioprobe is capable of binding to a redox reporter when hybridized to a nucleic acid sequence. In some embodiments, aggregation of the bioprobes, as compared to bioprobes lacking the charged functional group, is decreased by at least 10%, at least 20%, at least at least 30%, at least 40%, at least 50%, at least 60%, at least 70%, at least 80%, at least 90% or at least 100%. In yet other embodiments, the aggregation is decreased by between about 30% and about 90%, or by between about 50% and about 80%.

In some embodiments, a method for detecting a biomarker of interest is provided, the method comprising:
contacting the sample with a bio-probe comprising a nucleobase sequence capable of hybridizing to the biomarker of interest, and at least one charged functional group attached to said nucleobase sequence, wherein attachment of said charged functional group to said nucleobase results in lesser aggregation of a plurality of bio-probes; hybridizing the bio-probe to the biomarker; and
detecting the hybridization as being indicative of presence of the biomarker of interest in the sample.

In some embodiments, the charged functional group is a cationic functional group, an anionic functional group, a charged amino acid or a combination thereof. In some embodiments, the anionic functional group is a carboxylate, a sulfate or a sulfonate. In other embodiments, the cationic functional group is an amine or a guanadinum. In yet other embodiments, the amino acid is Asp, Glu, Aad, Ser, Lys, Orn, Dab, Dap, Arg, 4-phosphonomethyl-L-phenylalanine, 4-phosphonomethyl-D-phenylalanine, L-carboxyglutamic acid, D-carboxyglutamic acid, 5-Amino Salicylic Acid, or an amino acid shown in Table 2.

In still other embodiments, an increase in signal of at least 10%, at least 20%, at least 30%, at least 40%, at least 50% at least 60%, at least 70%, at least 80%, at least 90%, at least 100%, at least 125% or at least 150% over a control signal is detectable upon hybridization. In 30 other embodiments, an increase in signal of at least 20%-100% over a control signal is detectable upon hybridization. In still other embodiments, an increase in signal of at least 25%-50% over a control signal is detectable upon hybridization. In some embodiments, the bioprobes are immobilized onto a solid surface. In other embodiments, a plurality of bioprobes are immobilized onto distinct locations on the solid surface. In some embodiments, detection is performed by observing a reporter signal, and wherein a change in reporter signal on hybridization of the bio-probe with the biomaker, as compared to said reporter signal in the absence of hybridization of said bioprobe, is indicative of presence of said biomarker in the sample. In some embodiments, the reporter signal decreases on hybridization of the bio-probe with the biomarker. In some embodiments, the reporter signal decreases by about 10% to about 30% on hybridization of the bio-probe with the biomarker. In some embodiments, the reporter signal decreases by about 20% to about 50% on hybridization of bio-probe with the biomarker. In some embodiments, the reporter signal decreases by about 50% to about 100% on hybridization of bio-probe with the biomarker.

In some embodiments, the detection is by means of a fluorescent reporter group. In other embodiments, the detection is by means of a FRET system. In other embodiments, the detection is by means of a dye. In still other embodiments, the detection is by means of a redox reporter system, wherein the redox reporter system may be water-soluble. In some embodiments, the redox reporter group may comprise a metal, wherein the metal may be one of copper (Cu), cobalt (Co), palladium (Pd), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). In some embodiments, the nucleobase sequence is a DNA oligomer, an RNA oligomer or a PNA oligomer. In some embodiments, the aggregation of the bioprobe, as compared to bioprobes lacking the charged functional group, is decreased by at least 10%, at least 20%, at least 30%, at least 40%, at least 50%, at least 60%, at least 70%, at least 80%, at least 90% or at least 100%. In yet other embodiments, the aggregation is decreased by between 30%-90%, or by between 50%-80%.

In one embodiment, the target biomarker is DNA, RNA or a protein. In some embodiments, the sample may be a biological fluid, wherein the biological fluid may be selected from aqueous humour, vitreous humour, blood serum, breast milk, cerebrospinal fluid, cerumen, endolymph and perilymph, sastric juice, mucus (including nasal drainage and phlegm), peritoneal fluid, pleural fluid, saliva, sebum, semen, sweat, tears, vaginal secretion, vomit and urine.

A method for detecting the presence of a biomarker in an individual is also provided herein, the method comprising:
obtaining a biological fluid sample from the individual;
contacting the sample with a bio-probe comprising a nucleobase sequence capable of hybridizing to said biomarker, and at least one charged functional group attached to said nucleobase sequence; wherein attachment of said charged functional group to said nucleobase results in lesser aggregation of a plurality of bio-probes; hybridizing the bio-probe to the biomarker gene; and
detecting the hybridization as being indicative of presence of the biomarker in the individual.

Also provided herein are methods of detecting the presence of cancer cells in a biological sample, the method comprising:
contacting the sample with a bio-probe comprising a nucleobase sequence capable of hybridizing to a target biomarker, and at least one charged functional group attached to said nucleobase sequence; wherein attachment of said charged functional group to said nucleobase results in lesser aggregation of a plurality of bio-probes;
hybridizing the bio-probe to the target gene sequence; and
detecting the hybridization as being indicative of presence of cancer cells in the sample.

In some embodiments, the cancer cells detected are breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, melanoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas or epidermoid carcinomas.

In yet other embodiments, also provided are methods of detecting the presence of cancer cells in an individual, comprising:

obtaining a biological fluid sample from the individual;
contacting the sample with a bio-probe comprising a nucleobase sequence capable of hybridizing to a target biomarker, and at least one charged functional group attached to said nucleobase sequence, wherein attachment of said charged functional group to said nucleobase results in lesser aggregation of a plurality of bio-probes; hybridizing the bio-probe to the target gene sequence; and
detecting the hybridization as being indicative of presence of cancer cells in the sample.

In still other embodiments, provided are biosensors comprising:
an electrode; and
a bio-probe comprising a nucleobase sequence capable of hybridizing to a target biomarker, and at least one charged functional group attached to said nucleobase sequence, wherein attachment of said charged functional group to said nucleobase results in lesser aggregation of a plurality of bio-probes.

In yet other embodiments, provided are biosensing devices comprising:
a bio-probe comprising a nucleobase sequence capable of hybridizing to a target biomarker, and at least one charged functional group attached to said nucleobase sequence, wherein attachment of said charged functional group to said nucleobase results in lesser aggregation of a plurality of bio-probes; and
at least one redox active reporter.

In certain embodiments, the probe also comprises a peptide or a protein that is able to bind to or otherwise interact with a biomarker target (e.g. receptor or ligand) to provide an indication of the presence of the ligand or receptor in the sample. The probe may include a functional group (e.g., thiol, dithiol, amine, carboxylic acid) that facilitates binding with an electrode. Probes may also contain other features, such as longitudinal spacers, double-stranded and/or single-stranded regions, polyT linkers, double stranded duplexes as rigid linkers and PEG spacers.

In some embodiments, the bioprobe is bound or otherwise associated with a substrate. In some embodiments, the substrate may be a solid surface. In other embodiments, the substrate may be nitrocellulose, a nylon membrane, a glass plate, or polyvinyldifluoride ("PVDF"), a multiwell plate or other substrate, such as the tip of a light guide, optical fiber, conducting material or biosensor device. Further examples of substrates include materials that are comprised of a semiconductor material, such as silicon, silica, quartz, germanium, gallium arsenide, silicon carbide and indium compounds (e.g., indium arsenide, indium, antimonide and indium phosphide), selenium sulfide, ceramic, glass, plastic, polycarbonate or other polymer or combinations of any of the above. Substrates may optionally include a passivation layer, which is comprised of a material, which offers high resistance and maintains a small active surface area. Examples of appropriate materials include: silicon dioxide, silicon nitride, nitrogen doped silicon oxide (SiOxNy) or paralyene. In some embodiments, a linker or other spacer may be used to bind or otherwise associate the bioprobes disclosed herein with the substrate.

In some embodiments, the bioprobe is associated with an electrode. Electrodes may be comprised of a noble metal, (e.g., gold, platinum, palladium, silver, osmium, indium, rhodium, ruthenium); alloys of noble metals (e.g., gold-palladium, silver-platinum, etc.); conducting polymers (e.g., polypyrole (PPY)); non-noble metals (e.g., copper, nickel, aluminum, tin, titanium, indium, tungsten, platinum); metal oxides (e.g., zinc oxide, tin oxide, nickel oxide, indium tin oxide, titanium oxide, nitrogen-doped titanium oxide (TiOxNy); metal suicides (nickel suicide, platinum suicide); metal nitrides (titanium nitride (TiN), tungsten nitride (WN) or tantalum nitride (TaN)), carbon (nanotubes, fibers, graphene and amorphous) or combinations of any of the above.

In certain embodiments, the electrode is a microelectrode. Exemplary microelectrodes have a height in the range of about 0.5 to about 100 microns ($\mu m$), for example in the range of about 5 to about 20 microns (e.g., 10 microns); a diameter in the range of about 0.1 to about 500 microns, for example in the range of about 1 to about 100 microns, or for example in the range of about 1 to about 50 microns, or for example in the range of about 1 to about 1 microns. Microelectrodes can be any of a variety of shapes, including hemispherical, irregular (e.g., spiky), cyclical (wire-like) or fractal (e.g., dendritic). The surface of a microelectrode may be further coated or functionalized with a material which maintains the electrode's high conductivity, but facilitates binding with a probe.

In other embodiments, the electrode is a nanostructured microelectrode (NME). NMEs are electrodes, which are nanotextured and thus have an increased surface area. NMEs of the above-described materials are highly conductive and form strong bonds with the bioprobes. Exemplary NMEs have a height in the range of about 0.5 to about 100 microns ($\mu m$), for example in the range of about 5 to about 20 microns (e.g., 10 microns); a diameter in the range of about 1 to about 100 microns, for example in the range of about 1 to about 50 microns, or for example in 25 the range of about 1 to about 10 microns; and have nanoscale morphology (e.g., are nanostructured on a length scale of about 1 to about 300 nanometers and more preferably in the range of about 10 to about 20 nanometers). NMEs can be any of a variety of shapes, including hemispherical, irregular (e.g., spiky), cyclical (wire-like) or fractal (e.g., dendritic). The surface of an NME may be further coated or functionalized with a material, which maintains the electrode's high conductivity, but facilitates binding with a probe. For example, nitrogen containing NMEs (e.g., TiN, WN or TaN) can bind with an amine functional group of the probe. Similarly, silicon/silica chemistry as part of the NME can bind with a silane or siloxane group on the probe.

In a further embodiment a plurality of electrodes are arrayed on a substrate. Exemplary substrates are comprised of a semiconductor material, such as silicon, silica, quartz, germanium, gallium arsenide, silicon carbide and indium compounds (e.g., indium arsenide, indium, antimonide and indium phosphide), selenium sulfide, ceramic, glass, plastic, polycarbonate or other polymer or combinations of any of the above. Substrates may optionally include a passivation layer, which is comprised of a material, which offers high resistance and maintains a small active surface area. Examples of appropriate materials include: silicon dioxide, silicon nitride, nitrogen doped silicon oxide (SiOxNy) or paralyene. In certain embodiments, the plurality of electrodes are arrayed on the substrate, comprise bioprobes in conjunction with monolayer spacers, which minimize probe density, thereby maximizing complexation efficiency. Exemplary monolayer spacers have an affinity to metal and can be comprised, for example, of a thiol alcohol, such as mercaptohexanol, alkanethiols, cysteine, cystamine, thiol-amines, aromatic thiols (e.g., benzene thiol, dithiol), phosphonic acids or phosphinic acids.

The present disclosures may comprise in its embodiments any addressable array technology known in the art. One embodiment of polynucleotide arrays has been generally described in U.S. Pat. No. 5,143,854; PCT publications WO 90/15070 and 92/10092. These arrays may generally be produced using mechanical synthesis methods or light directed synthesis methods, which incorporate a combination of photolithographic methods and solid phase oligonucleotide synthesis. (Fodor et al, Science, 251:767-777, (1991)). The immobilization of arrays of oligonucleotides on solid supports has been rendered possible by the development of a technology generally identified as "Very Large Scale Immobilized Polymer Synthesis" in which, typically, probes are immobilized in a high density array on a solid surface of a chip. Examples of such technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies to order and display the oligonucleotide arrays on the chips in an attempt to maximize hybridization patterns and sequence information are disclosed in PCT Publications WO 94/12305, WO 94/11530, WO 97/29212 and WO 97/31256.

In certain embodiments are methods of detecting a biomolecule or a biomarker, using the bioprobes and biosensing devices described herein. The method involves contacting a purified or unpurified sample with a biosensing device that comprises a bio-probe comprising a nucleobase sequence capable of hybridizing to the target biomarker of interest, and at least one charged functional group, including a cationic functional group, a anionic functional group or a charged amino acid, attached to said nucleobase sequence; hybridizing the bio-probe to the target biomarker; and detecting the hybridization as being indicative of presence of the biomarker of interest in the sample. In certain embodiments, this detection is performed by means of a redox-active reporter. In certain embodiments, this method is used to detect the presence of target biomolecules in solutions, such as biological fluids obtained from a test subject. These biological fluids include, but are not limited to aqueous humour, vitreous humour, blood serum, breast milk, cerebrospinal fluid, cerumen (earwax), endolymph and perilymph, sastric juice, mucus (including nasal drainage and phlegm), peritoneal fluid, pleural fluid, saliva, sebum (skin oil), semen, sweat, tears, vaginal secretion, vomit and urine.

In some embodiments, is provided a method of identification of a specific biomolecule (e.g., nucleic acids) within a population of heterogeneous biomolecules. The method comprises contacting a bio-probe comprising a nucleobase sequence capable of hybridizing to the target biomolecule of interest, and at least one charged amino acid attached to said nucleobase sequence; hybridizing the bio-probe to the target biomolecule; and detecting the hybridization as being indicative of presence of the biomolecule of interest.

In certain embodiments are methods of diagnosing a disease or condition in a subject, using the bioprobes and biosensing devices described supra. In certain embodiments, the disease is a cancer. In certain embodiments is a method of detecting the presence of cancer cells in a biological sample, comprising: contacting the sample with a bio-probe comprising a nucleobase sequence capable of hybridizing to a target biomarker, and at least one charged amino acid attached to said nucleobase sequence; hybridizing the bio-probe to the target gene sequence; and detecting the hybridization as being indicative of presence of cancer cells in the sample.

In some embodiments, the cancer being diagnosed or detected is selected from the group consisting of breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach/bronchi, kidneys, basal cell carcinoma, squamous cell carcinoma of both ulcerating and papillary type, metastatic skin carcinoma, melanoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas. In other embodiments, the cancer is pancreatic cancer, liver cancer, breast cancer, osteosarcoma, lung cancer, soft tissue sarcoma, cancer of the larynx, melanoma, ovarian cancer, brain cancer, Ewing's sarcoma or colon cancer.

In certain embodiments are methods of detecting a pathogen using the bioprobes and biosensing devices described herein. In certain embodiments, the pathogen is a bacteria, a virus, a fungus or a parasite. In certain embodiments is a method of detecting the presence of a pathogen in a biological sample, comprising: contacting the sample with a bio-probe comprising a nucleobase sequence capable of hybridizing to a target biomarker, and at least one charged amino acid attached to said nucleobase sequence; hybridizing the bio-probe to the target gene sequence; and detecting the hybridization as being indicative of presence of a pathogen, including a bacteria, a virus, a fungus, or a parasite, in the sample.

The embodiments of the multiplexing methods disclosed herein can be used to screen a single individual against a battery of the bio-probes described herein. Accordingly, different types of bio-probes may be labeled with different reporters so that the presence of multiple bioprobes bound to target biomolecules from a biological sample from the individual can be accomplished. Alternatively, the different bioprobes may be attached to distinct positions on a solid substrate, such that detection of bioprobes bound to specific target biomolecules form a biological sample from the individual can be discerned. A biological sample from the individual to be screened is obtained and prepared and the biomolecules to be probed are disposed on a support. The various bioprobes are contacted with the biomolecules, the unbound and nonspecifically bound probes are removed by washing, and the signals are detected and resolved.

Definitions

Unless defined otherwise, all technical and scientific terms used herein have the same meaning as is commonly understood by one of skill in the art to which the technology belongs. All patents, patent applications, published applications and publications, Genbank sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the term "nucleobase" as used herein, is intended to by synonymous with "nucleic acid base or mimetic thereof" In general, a nucleobase is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, and 10 alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine 15 and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1-H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido(3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer 25 Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993.

Modified nucleobases include, but are not limited to, universal bases, hydrophobic bases, 30 promiscuous bases, size-expanded bases, and fluorinated bases as defined herein. Certain of these nucleobases are particularly useful for increasing the binding affinity of the oligomeric compounds disclosed herein. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently base substitutions, even more particularly when combined with 2'-0-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941 each of which is herein incorporated by reference.

The term "nucleobase" also encompasses polymers having additional substituents including, without limitation, protein groups, lipophilic groups, intercalating agents, diamines, folic acid, cholesterol and adamantane. The term "nucleobase" also encompasses any other nucleobase containing polymer, including, without limitation, peptide nucleic acids (PNA), peptide nucleic acids with phosphate groups (PHONA), locked nucleic acids (LNA), morpholino nucleic acids, methyl phosphonate nucleic acids, and oligonucleotides having backbone sections with alkyl linkers or amino linkers.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified nucleotides, such as, but are not limited to, phosphorothioate nucleotides and deazapurine nucleotides and other nucleotide analogs.

As used herein, the term "subject" refers to animals, plants, insects, and birds. Included are higher organisms, such as mammals and birds, including humans, primates, rodents, cattle, pigs, rabbits, goats, sheep, mice, rats, guinea pigs, cats, dogs, horses, chicken and others.

As used herein, "selectable or screenable markers" confer an identifiable change to a cell permitting easy identification of cells containing an expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

As used herein, "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "host cell" denotes, for example, microorganisms, yeast cells, insect cells, and mammalian cells, that can be, or have been, used as recipients for multiple constructs for producing a targeted delivery vector. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

The term "moiety" refers to a specific segment or functional group of a molecule. Chemical moieties are often recognized as chemical entities embedded in or appended to a molecule.

The term "solid support" refers to supports used for anchoring the bioprobes described herein. The solid support can be a solid surface such as nitrocellulose, a nylon membrane, a glass plate, a resin, nanoparticles, nanocrystals, microparticles, semi-conductor material or an electrode.

The term "linking moiety" refers to any moiety optionally positioned between the terminal nucleoside and the solid support or between the terminal nucleoside and another nucleoside, nucleotide, or nucleic acid.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and 15 transcription termination sequence is, usually, be located 3' to the coding sequence. The term "non-coding sequence" or "non-coding region" refers to regions of a polynucleotide sequence that are not translated into amino acids (e.g., 5' and 3' un-translated regions).

The term "reading frame" refers to one of the six possible reading frames, three in each direction, of the double stranded DNA molecule. The reading frame that is used determines which codons are used to encode amino acids within the coding sequence of a DNA molecule.

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

The term "base pair" or ("bp"): a partnership of adenine (A) with thymine (T), or of cytosine (C) with guanine (G) in a double stranded DNA molecule. In RNA, uracil (U) is substituted for thymine.

As used herein a "codon" refers to the three nucleotides which, when transcribed and translated, encode a single amino acid residue; or in the case of UUA, UGA or UAG encode a termination signal. Codons encoding amino acids are well known in the art and are provided for convenience herein in Table 1.

TABLE 1

Codon Usage Table

| Codon | Amino acid | AA | Abbr. | Codon | Amino acid | AA | Abbr. |
|---|---|---|---|---|---|---|---|
| UUU | Phenylalanine | Phe | F | UCU | Serine | Ser | S |
| UUC | Phenylalanine | Phe | F | UCC | Serine | Ser | S |
| UUA | Leucine | Leu | L | UCA | Serine | Ser | S |
| UUG | Leucine | Leu | L | UCG | Serine | Ser | S |
| CUU | Leucine | Leu | L | CCU | Proline | Pro | P |
| CUC | Leucine | Leu | L | CCC | Proline | Pro | P |
| CUA | Leucine | Leu | L | CCA | Proline | Pro | P |
| CUG | Leucine | Leu | L | CCG | Proline | Pro | P |
| AUU | Isoleucine | Ile | I | ACU | Threonine | Thr | T |
| AUC | Isoleucine | Ile | I | ACC | Threonine | Thr | T |
| AUA | Isoleucine | Ile | I | ACA | Threonine | Thr | T |
| AUG | Methionine | Met | M | ACH | Threonine | Thr | T |
| GUU | Valine | Val | V | GCU | Alanine | Ala | A |
| GUC | Valine | Val | V | GCC | Alanine | Ala | A |
| GUA | Valine | Val | V | GCA | Alanine | Ala | A |
| GUG | Valine | Val | V | GCG | Alanine | Ala | A |
| UAU | Tyrosine | Tyr | Y | UGU | Cysteine | Cys | C |
| UAC | Tyrosine | Tyr | Y | UGC | Cysteine | Cys | C |
| UUA | | Stop | | UGA | | Stop | |

TABLE 1-continued

Codon Usage Table

| Codon | Amino acid | AA | Abbr. | Codon | Amino acid | AA | Abbr. |
|---|---|---|---|---|---|---|---|
| UAG | | Stop | | UGG | Tryptophan | Trp | W |
| CAU | Histidine | His | H | CGU | Arginine | Arg | R |
| CAC | Histidine | His | H | CGC | Arginine | Arg | R |
| CAA | Glutamine | Gln | Q | CGA | Arginine | Arg | R |
| CAG | Glutamine | Gln | Q | CGG | Arginine | Arg | R |
| AAU | Asparagine | Asn | N | AGU | Serine | Ser | S |
| AAC | Asparagine | Asn | N | AGC | Serine | Ser | S |
| AAA | Lysine | Lys | K | AGA | Arginine | Arg | R |
| AAG | Lysine | Lys | K | AGG | Arginine | Arg | R |
| GAU | Aspartate | Asp | D | GGU | Glycine | Gly | G |
| GAC | Aspartate | Asp | D | GGC | Glycine | Gly | G |
| GAA | Glutamate | Glu | E | GGA | Glycine | Gly | G |
| GAG | Glutamate | Glu | E | GGG | Glycine | Gly | G |

As used herein, a "wobble position" refers to the third position of a codon. Mutations in a DNA molecule within the wobble position of a codon, in some embodiments, result in silent or conservative mutations at the amino acid level. For example, there are four codons that encode Glycine, i.e., GGU, GGC, GGA and GGG, thus mutation of any wobble position nucleotide, to any other nucleotide, does not result in a change at the amino acid level of the encoded protein and, therefore, is a silent substitution.

As used herein, a "silent substitution" or "silent mutation" is one in which a nucleotide within a codon is modified, but does not result in a change in the amino acid residue encoded by the codon. Examples include mutations in the third position of a codon, as well in the first position of certain codons such as in the codon "CGG" which, when mutated to AGG, still encodes Arg.

The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

As used herein, a "complementary DNA" or "cDNA" includes recombinant polynucleotides synthesized by reverse transcription of mRNA and from which intervening sequences (introns) have been removed.

"Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 50% identity, less than 40% identity, less than 35% identity, less than 30% identity, less than 25% identity, less than 20% identity, less than 15% identity or less than 10% identity with a sequence described herein. In comparing two sequences, the absence of residues (amino acids or nucleic acids) or presence of extra residues also decreases the identity and homology/similarity.

The term "homology" may describe a mathematically based comparison of sequence similarities which is used to identify genes with similar functions or motifs. The nucleic acid sequences described herein can be used as a "query sequence" to perform a search against public databases, for example, to identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25:

3389-3402 (1997)). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403-410 (1990). The well-known Smith Waterman algorithm can also be used to determine identity.

A "heterologous" region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

The term "transition mutations" refers to base changes in a DNA sequence in which a pyrimidine (cytidine (C) or thymidine (T) is replaced by another pyrimidine, or a purine (adenosine (A) or guanosine (G) is replaced by another purine.

The term "transversion mutations" refers to base changes in a DNA sequence in which a pyrimidine (cytidine (C) or thymidine (T) is replaced by a purine (adenosine (A) or guanosine (G), or a purine is replaced by a pyrimidine.

Nucleobases and Modified Nucleobases

The nucleobases used herein are natural nucleobases or modified nucleobases derived 30 from natural nucleobases. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu et al. RNA 9: 1034-1048 (2003), Limbach et al., *Nucleic Acids Research* 22: 2183-2196 (1994) are also contemplated as nucleobase moieties.

Compounds represented by the following general formulae are also contemplated as modified nucleobases:

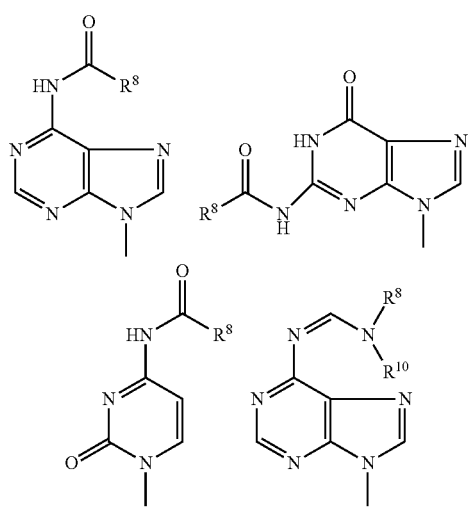

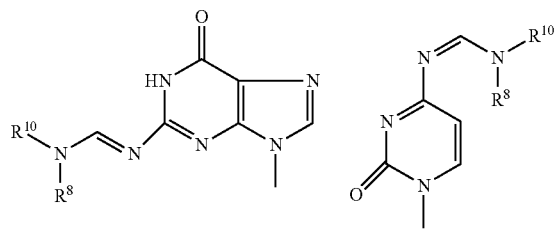

In the formulae above, $R^8$ is a linear or branched alkyl, aryl, aralkyl, or aryloxylalkyl group having 1 to 15 carbon atoms, including, by way of example only, a methyl, isopropyl, phenyl, benzyl, or phenoxymethyl group; and each of R9 and R10 represents a linear or branched alkyl group having 1 to 4 carbon atoms.

Modified nucleobases also include expanded-size nucleobases in which one or more benzene rings has been added. Nucleic base replacements described in the Glen Research catalog (www.glenresearch.com); Krueger A T et al., *Acc. Chem. Res.* 40: 141-150 (2007); Kool, E T. *Acc. Chem. Res.* 35: 936-943 (2002); Benner S. A., et al., *Nat. Rev. Genet.* 6: 553-543 (2005); Romesberg, F. E., et al., *Curr. Opin. Chem. Biol.* 7, 723-733 (2003, are contemplated as useful for the synthesis of the nucleic acids described herein. Some examples of these expanded-size nucleobases are shown below:

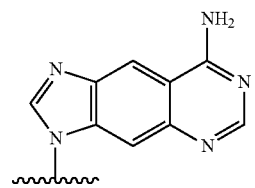

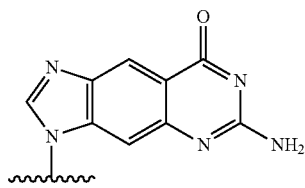

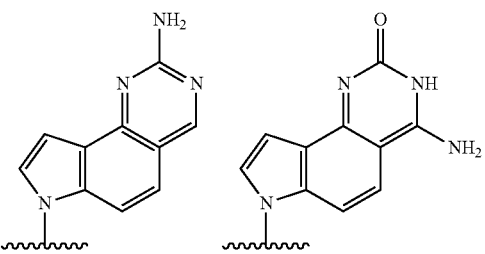

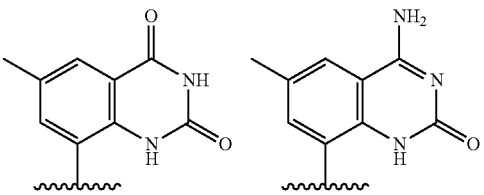

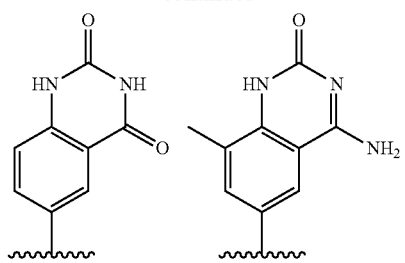

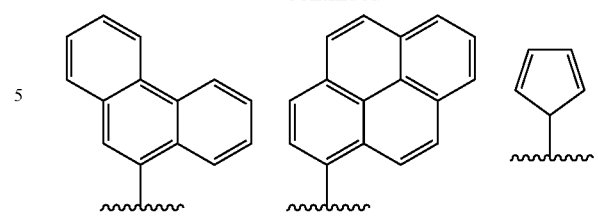

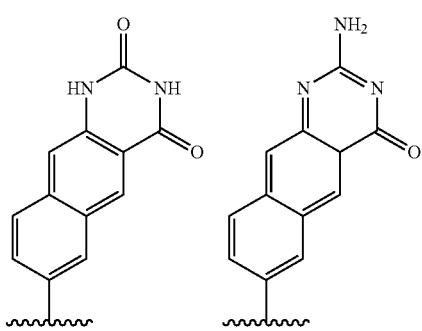

Modified nucleobases which are fluorescent are also contemplated. Non-limiting examples of these base replacements include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

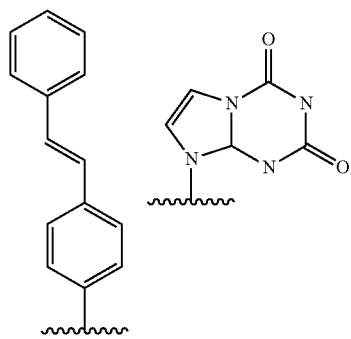

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, *Org. Lett.* 4: 4377-4380 (2002). Shown below is an example of a porphyrin-derived ring which can be used as a base replacement:

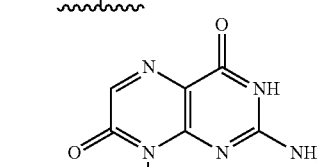

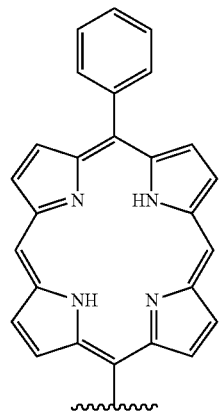 [SMILES: *c1c2nc(cc3ccc([nH]3)c(-c3ccccc3)c3nc(cc4ccc1[nH]4)C=C3)C=C2]

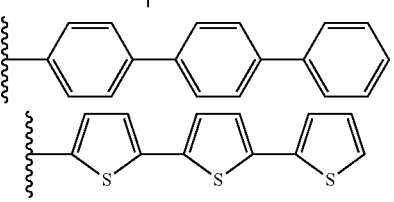

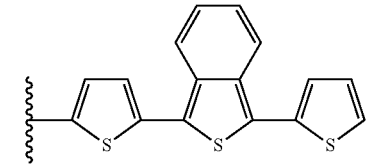

Other modified nucleobases also include base replacements such as those shown below:

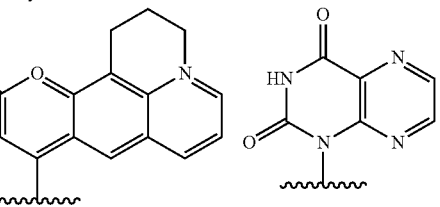

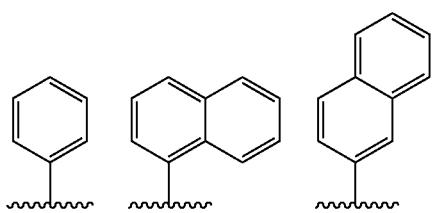

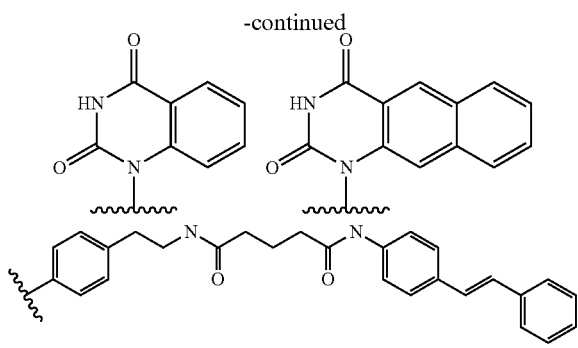

The modified nucleobases can be unsubstituted or contain further substitutions such as heteroatoms, alkyl groups, or linking moieties connected to fluorescent moieties, biotin or avidin moieties, or other protein or peptides. Modified nucleobases also include certain 'universal bases' that are not nucleobases in the most classical sense, but function similarly to nucleobases. One representative example of such a universal base is 3-nitropyrrole.

In some embodiments, the nucleobases or modified nucleobases comprises biomolecule binding moieties such as antibodies, antibody fragments, biotin, avidin, streptavidin, receptor ligands, or chelating moieties. In other embodiments, the nucleobases may be 5-bromouracil, 5-iodouracil, or 2,6-diaminopurine. In yet other embodiments, the nucleobase is modified by substitution with a fluorescent or biomolecule binding moiety. In some embodiments, the substituent on the nucleobase is a fluorescent moiety. In other embodiments, the substituent is biotin or avidin.

Bioprobes Comprising Nucleobases

Generally speaking, it is possible to identify sequence-specific nucleic acid segments, and to design sequences complementary to those segments, thereby creating a specific probe for a target cell, such as different pathogen cells or mammalian cells that have, for example, mutated from their normal counterparts. In principle, one can design complementary sequences to any identified nucleic acid segment. In many instances, unique sequences specific to an organism may be used as probes for a particular organism or cell type. The quantitative phenotypic analysis of yeast deletion mutants, for example, has utilized unique nucleic acid sequence identifiers to analyze deletion strains by hybridization with tagged probes using a high-density parallel array.

Hybridization involves joining a single strand of nucleic acid with a complementary probe sequence. Hybridization of a nucleobase comprising bioprobe to nucleic acid sequences such as gene sequences from bacteria, or viral DNA (or RNA) offers a very high degree of accuracy for identifying nucleic acid sequences complementary to the probe. Nucleic acid strands tend to be paired to their complements in double-stranded structures. Thus, a single-stranded nucleobase comprising molecule will seek out its complement in a complex mixture of DNA and/or RNA containing large numbers of other nucleic acid molecules. Nucleobase based bioprobe detection methods can be very specific to nucleic acid sequences. Factors affecting the hybridization or reassociation of two complementary nucleic acid strands include temperature, contact time, salt concentration, degree of mismatch between the base pairs, and the length and concentration of the target and probe sequences.

The DNA, RNA, PNA, morpholino nucleic acid, or methyl phosphonate nucleic acid comprising biosensors disclosed herein may be used for their ability to selectively form duplex molecules with complementary stretches of DNA or RNA fragments. In one embodiment, provided are methods for detecting particular nucleic acid sequences in a sample. The method generally involves obtaining a sample suspected of containing the polynucleotide of interest; contacting the sample with a bioprobe that comprises an isolated nucleobase sequence substantially complementary to the nucleic acid sequence of interest; at least one charged amino acid attached to said nucleobase sequence; and a suitable detector, under conditions effective to allow hybridization; and detecting the hybridization. In some embodiments, the methods are used for detecting changes in a nucleotide sequence, for example, single-nucleotide polymorphisms or mutations. The methods generally comprise obtaining a sample suspected of containing the polynucleotide of interest; contacting the sample with a bioprobe that comprises an isolated nucleobase sequence; at least one charged amino acid attached to said nucleobase sequence; and a suitable detector, under conditions effective to allow hybridization; quantifying or measuring said hybridization and comparing against a standard or control hybridization sample.

Bioprobes Comprising Peptide Nucleic Acid

DNA and RNA have a deoxyribose and ribose sugar backbone, respectively, whereas PNA's backbone is composed of repeating N-(2-aminoethyl)-glycine units linked by peptide bonds. PNA is not known to occur naturally. The various purine and pyrimidine bases are linked to the backbone by methylene carbonyl bonds. PNAs are depicted like peptides, with the N-terminus at the first (left) position and the C-terminus at the right.

Since the backbone of PNA contains no charged phosphate groups, the binding between PNA/DNA strands is stronger than between DNA/DNA strands due to the lack of electrostatic repulsion. Early experiments with homopyrimidine strands (strands consisting of only one repeated pyrimidine base) have shown that the Tm ("melting" temperature) of a 6-base thymine PNA/adenine DNA double helix was 31° C. in comparison to an equivalent 6-base DNA/DNA duplex that denatures at a temperature less than 10° C. Mixed base PNA molecules are true mimics of DNA molecules in terms of base-pair recognition. PNA/PNA binding is stronger than PNA/DNA binding.

Synthetic peptide nucleic acid oligomers have been used in recent years in molecular biology procedures, diagnostic assays and antisense therapies. Due to their higher binding strength it is not necessary to design long PNA oligomers for use in these roles, which usually require oligonucleotide probes of 20-25 bases. The main concern of the length of the PNA-oligomers is to guarantee the specificity. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. Though an unmodified PNA cannot readily cross cell membranes to enter the cytosol, covalently coupling a 5 cell penetrating peptide to a PNA can improve cytosolic delivery.

The length of the PNA probes is optimized for the specific intended use. The optimal length is a function of the distribution of purine and pyrimidine bases and in contrast to nucleotide probes is less dependent on salt concentration and pH as regulators of the stringency of the hybridization conditions.

The PNA based bioprobes may comprise one or more labelling groups connected to the glycine nitrogen for internal labelling of the PNA probes or one or more labelling groups connected to one or both ends of the bioprobe provided that the labelling group does not destroy the performance of the probe. As used herein, the term "label" or "labelling group" means a substituent, which is useful for detecting a bioprobe.

In many instances, the label is attached to the C-terminal and/or N-terminal end of the PNA bioprobe using suitable linkers. Generally, all chemical methods for N- or C-terminal labelling of peptides and for 5' or 3' end labelling of DNA and/or RNA which are presently known may in general terms be applied to PNAs also. For maximum stability, particularly at alkaline pH, the N-terminus of the PNA may be blocked, e.g., with an amino acid such as lysine or glycine.

Alternatively, the N-terminus may be modified by a label, an acetyl group or by a saturated or unsaturated aliphatic group, an aromatic group, a heteroaromatic group, a saturated or unsaturated cyclic group and/or a saturated or unsaturated heterocyclic group which may optionally be substituted by one or more heteroatom-containing groups, such as OH, NH2, SO2, SH and COOH. This type of modification prevents gradual intra-molecular rearrangement of the N-terminal residue. The use of PNA as a probe molecule has been shown previously to increase the sensitivity of biosensing assays and is particularly advantageous in electrochemical assays because it produces lowered background currents.

PNA probes, which carry no molecular charge at neutral pH, offer many advantages when used for biosensing. One key advantage is the increase in binding affinity for target DNA or RNA sequences (O. Brandt, J. D. Hoheisel, Trends Biotech. 22: 617 (2004)). Moreover, when sensing schemes are used that rely on changes in surface charge upon the binding of a nucleic acid to a sensor, lowered background signals, and consequently improved limits of detection, can be obtained because of the absence of charge in the probe. Owing to this effect, our electro-catalytic reporter system, which relies on the attraction of ruthenium ions to the sensor surface by nucleic acids captured by immobilized probe molecules, has been shown to exhibit better sensitivity when PNA probes are used (Z. Fang, S. O. Kelley, Anal. Chem. 81:612 (2009)).

However, there are drawbacks to the use of PNA probes. In the present study, it was seen that where there are stringent requirements on the specific sequence employed—i.e. the molecular probe must target a specific fusion sequence—the PNA bioprobes were found not to participate in hybridization when immobilized on biosensors; moreover, precipitation out of solution of the original probe was observed. From these observations, it was apparent that the bioprobe sequence was prone to aggregation. We concluded that the specific sequence mandated 10 by this particular biosensing application was not usable when synthesized as a neutral molecule.

Ribozymes are enzymatic RNA molecules that cleave particular mRNA species. In certain embodiments, ribozymes capable of cleaving RNA segments, and the resulting detection of such mRNAs or ribozymes, may be used herein with the methods and the DNA, RNA and/or PNA based bioprobes disclosed herein.

Six basic varieties of naturally-occurring enzymatic RNAs are known presently. Each can catalyze the hydrolysis of RNA phosphodiester bonds (and thus can cleave other RNA molecules) under physiological conditions. In general, enzymatic nucleic acids act by first binding to a target RNA. Such binding occurs through the target binding portion of enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis-δ virus, group I intron or RNaseP RNA (in association with an RNA guide sequence) or Neurospora VS RNA motif. Examples of hammerhead motifs are described by Rossi et al. (1992); examples of hairpin motifs are described by Hampel et al. (Eur. Pat. EP 0360257), Hampel and Tritz (1989), Hampel et al. (1990) and Cech et al. (U.S. Pat. No. 5,631,359); an example of the hepatitis-6 virus motif is described by Perrotta and Been (1992); an example of the RNaseP motif is described by Guerrier-Takada et al. (1983); and an example of the Group I intron is described by Cech et al. (U.S. Pat. No. 4,987,071). Contemplated herein are nucleobase comprising bioprobes having a specific substrate binding site which is complementary to one or more of the target gene RNA regions, and having a nucleotide sequences within or surrounding that substrate binding site which impart an RNA cleaving activity to the molecule.

Bioprobes Comprising Charged Functional Groups

The bioprobes disclosed herein comprise at least one charged functional group attached to a nucleobase sequence capable of hybridizing to a target molecule. In some embodiments, the charged functional group is a cationic functional group, an anionic functional group or a charged amino acid. In some embodiments, the anionic functional group is a carboxylate, a sulfate or a sulfonate. In certain embodiments, the cationic functional group is an amine or guanadinum group. In some embodiments, the charged functional group is a charged amino acid.

A charged amino acid is an amino acid that is either positively charged (protonated), or negatively charged (deprotonated) at physiological pH. Naturally occurring negatively charged amino acids include Aspartic acid (Asp, D) and Glutamic acid (Glu, E). Naturally occurring positively charged amino acids include Lysine (Lys, K) and Arginine (Arg, R). An amino acid that is sometimes protonated at physiological pH is Histidine (His, H).

In addition to the above, other charged amino acids including, but not restricted to Ornithine (Orn, O), Diaminobutyric acid (Dab), Diamino-propionic acid (Dap), and Aminoadipic acid (Aad). Additional charged amino acids are provided in table 2.

TABLE 2

Anionic Amino Acids

| Amino Acid | Peptide monomer (Example) | Full name | Structure |
|---|---|---|---|
| L-aspartic acid | Fmoc-Asp(OBut)-OH | Fmoc-L-aspartic acid β-t-butyl ester | 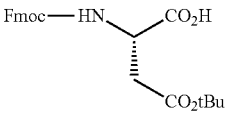 |
| D-aspartic acid | Fmoc-D-Asp(OBut)-OH | N-α-Fmoc-D-aspartic acid β-t.-butyl ester | 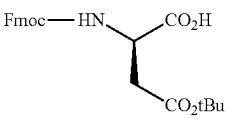 |
| L-glutamic acid | Fmoc-Glu(OBut)-OH | Fmoc-L-glutamic acid γ-t-butyl ester | 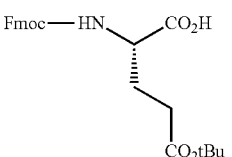 |
| D-glutamic acid | Fmoc-D-Glu(OBut)-OH | N-α-Fmoc-D-glutamic acid γ-t.-butyl ester | 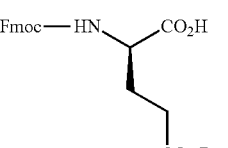 |
| 5-Amino Salicylic Acid | Boc-5-Amino Salicyclic Acid | | 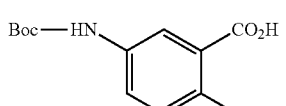 |
| D-γ-carboxy-glutamic acid | Fmoc-D-Gla(OBut)$_2$-OH | | 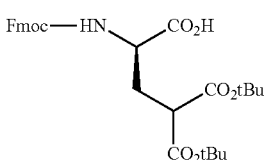 |
| L-γ-carboxy-glutamic acid | Fmoc-Gla(OBut)$_2$-OH | Fmoc-L-γ-carboxyglutamic acid γ,γ-di-t-butyl ester | 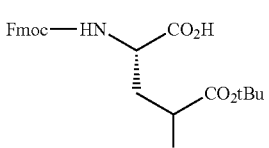 |
| 4-phosphono methyl-D-phenylalanine | Fmoc-D-Pmp-OH | Fmoc-4-phosphonomethyl-D-phenylalanine | 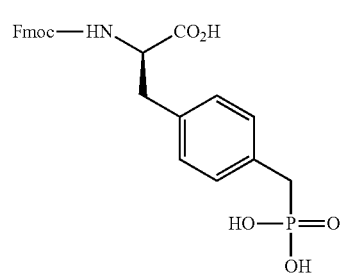 |

TABLE 2-continued

Anionic Amino Acids

| Amino Acid | Peptide monomer (Example) | Full name | Structure |
| --- | --- | --- | --- |
| 4-phosphonomethyl-L-phenylalanine | Fmoc-Pmp-OH | Fmoc-4-phosphonomethyl-L-phenylalanine | 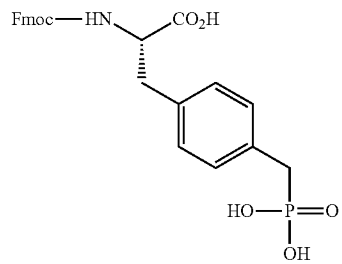 |
| L-phosphoserine | Fmoc-Ser(PO(OBzl)OH)-OH | N-α-Fmoc-O-benzyl-L-phosphoserine | 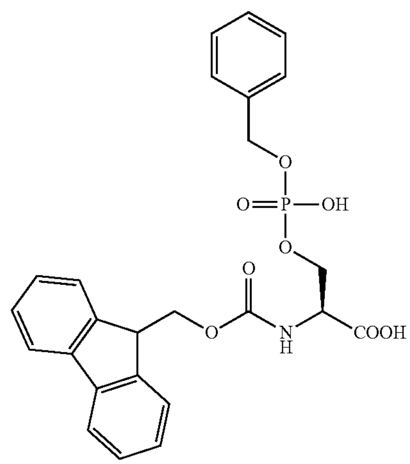 [SMILES: O=C(N[C@@H](COP(=O)(O)OCc1ccccc1)C(=O)O)OCC1c2ccccc2-c2ccccc21] |
| D-phosphoserine | Fmoc-D-Ser(PO(OBzl)OH-OH | N-α-Fmoc-O-benzyl-D-phosphoserine | 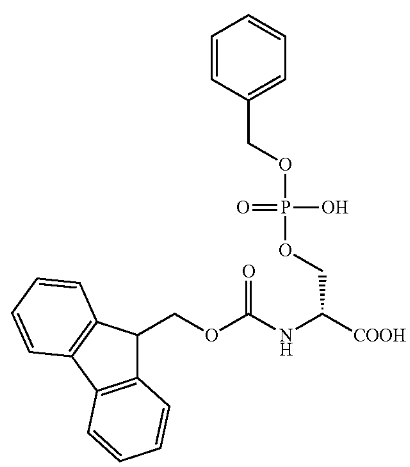 [SMILES: O=C(N[C@H](COP(=O)(O)OCc1ccccc1)C(=O)O)OCC1c2ccccc2-c2ccccc21] |

TABLE 2-continued

Anionic Amino Acids

| Amino Acid | Peptide monomer (Example) | Full name | Structure |
|---|---|---|---|
| L-phospho-threonine | Fmoc-Thr(PO(OBzl)OH)-OH | N-α-Fmoc-O-benzyl-L-phosphothreonine | 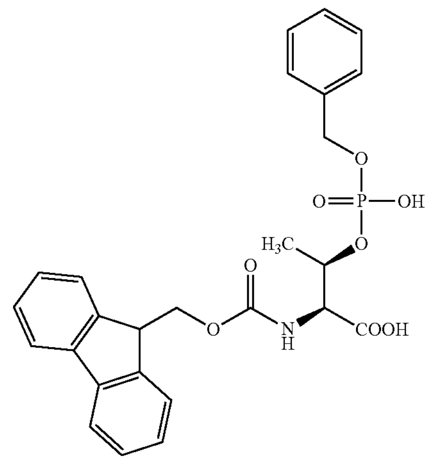 [SMILES: C[C@@H](OP(=O)(O)OCc1ccccc1)[C@H](NC(=O)OCC1c2ccccc2-c2ccccc21)C(=O)O] |
| D-phospho-threonine | Fmoc-D-Thr(PO(OBzl)OH)-OH | N-α-Fmoc-O-benzyl-D-phosphothreonine | 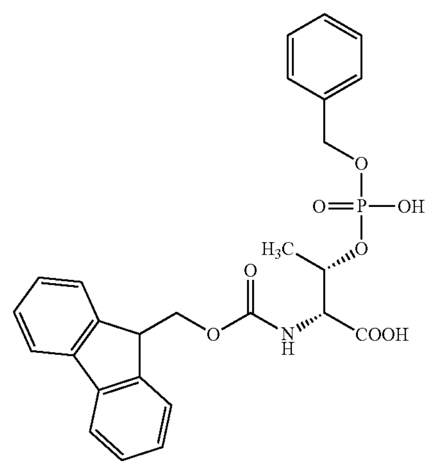 [SMILES: C[C@H](OP(=O)(O)OCc1ccccc1)[C@@H](NC(=O)OCC1c2ccccc2-c2ccccc21)C(=O)O] |
| O-phospho-L-tyrosine | Fmoc-Tyr(PO$_3$H$_2$)-OH | N-α-Fmoc-O-phospho-L-tyrosine | 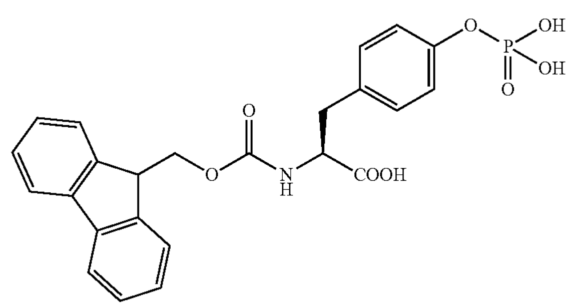 [SMILES: O=C(N[C@@H](Cc1ccc(OP(=O)(O)O)cc1)C(=O)O)OCC1c2ccccc2-c2ccccc21] |

TABLE 2-continued

Anionic Amino Acids

| Amino Acid | Peptide monomer (Example) | Full name | Structure |
|---|---|---|---|
| O-benzyl-L-phospho-tyrosine | Fmoc-Tyr(PO(OBzl)OH)-OH | N-α-Fmoc-O-benzyl-L-phosphotyrosine | 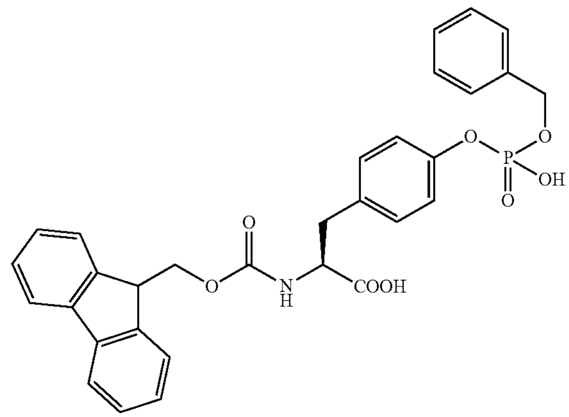 [SMILES: O=C(N[C@@H](Cc1ccc(OP(=O)(O)OCc2ccccc2)cc1)C(=O)O)OCC1c2ccccc2-c2ccccc21] |
| O-benzyl-D-phospho-tyrosine | Fmoc-D-Tyr(PO(OBzl)OH)-OH | N-α-Fmoc-O-benzyl-D-phosphotyrosine | 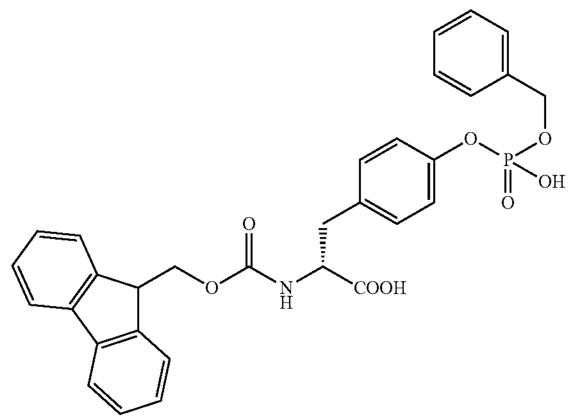 [SMILES: O=C(N[C@H](Cc1ccc(OP(=O)(O)OCc2ccccc2)cc1)C(=O)O)OCC1c2ccccc2-c2ccccc21] |
| O-sulfo-L-tyrosine | Fmoc-Tyr(SO3•NnBu$_4$)-OH | N-a-Fmoc-O-sulfo-L-tyrosine tetrabutylammonium salt | 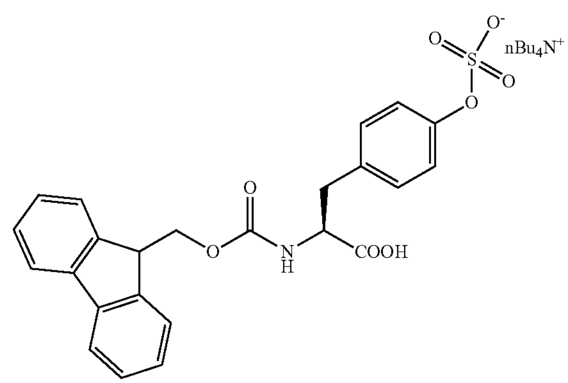 [SMILES: O=C(N[C@@H](Cc1ccc(OS(=O)(=O)[O-])cc1)C(=O)O)OCC1c2ccccc2-c2ccccc21 ; "nBu4N+"] |

Herein, we have generated bioprobe molecules that exhibit improved water solubility and monolayer-forming properties with little or no aggregation. The strategy used is the introduction of a charged functional group at the termini of the nucleobase sequence to beneficially alter the probe's properties. Attachment of charged functional groups, including cationic functional groups, anionic functional groups and charged amino acids, to PNA, DNA, RNA, or modified nucleic acids is achieved using coupling chemistry similar to that used in traditional PNA synthesis. This subtle modification—the inclusion of sufficient charged functional groups—improves the behaviour of the nucleobase comprising bioprobe in that solubility in aqueous solution is improved, and exhibited better performance when used to detect the target biomolecule of interest. In some embodiments, the inclusion of at least one charged functional group results in a decrease in aggregation, as compared to the absence of the at least one charged functional group, of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In some embodiments, the inclusion of at least one charged functional group results in a decrease in aggregation, as compared to the absence of the at least one charged functional group, of at least between about 10% and about 90%, at least between about 20% and about 80%, at least between about 30% and about 70%, at least between about 30% and about 90%, at least between about 40% and about 70%, at least between about 50% and about 80%, at least between about 50% and about 70% or at least between about 60% and about 90%. In some embodiments, the inclusion of at least one charged functional group results in a decrease in aggregation, as compared to the absence of the at least one charged functional group, of at least between 10% and 90%, at least between 20% and 80%, at least between 30% and 70%, at least between 30% and 90%, at least between 40% and 70%, at least between 50% and 80%, at least between 50% and 70% or at least between 60% and 90%.

Depending on the severity of the aggregation, a number of charged functional groups can be used in the bioprobe. In some cases, the placement of one or more charged functional groups, including cationic functional groups, anionic functional groups and charged amino acids, at the termini of the nucleobase sequence is sufficient to achieve a robust, selective bioprobe. In certain embodiments, the number of charged functional groups can be as many as the total number of nucleobases in the bioprobe sequence. The charged functional groups, including cationic functional groups, anionic functional groups and amino acids, can be positioned at one or both terminii of the nucleobase sequence, or the charged functional groups can be placed intermittently through the sequence either individually, or in groups of two, three or more, as seen in FIG. 2.

Immobilization of bioprobes on a multiarray (e.g., those of up to about 100 or about 200, or about 400, or even about 1000 or so channels) sampling platform can be performed onto a transducer detection surface to ensure optimal contact and maximum detection. When immobilized onto a substrate, the bioprobes are stabilized and, therefore, can be reused repetitively. In one illustrative embodiment, the hybridization is performed on an immobilized target or a probe molecule attached on a solid surface such as a nitrocellulose, a nylon membrane, a glass plate, or polyvinyldifluoride ("PVDF"), a multiwell plate or another convenient substrate, such as the tip of a light guide, optical fiber, conducting material or biosensor device, that lends itself to this purpose. In some embodiments, also included is an array device comprising multiple bioprobes affixed to a solid matrix as described herein, or suspended in solution in a linear or multidimensional format. In another aspect the bioprobes are affixed to the solid matrix in a specific array format or are placed within specific wells of a multiwell plate. Alternatively, in some embodiments, the bioprobes can be immobilized on resins, nanoparticles, nanocrystals, or microparticles.

Electrodes

In some embodiments, a nucleic acid hybridization detection assay is carried out at a solid electrode surface. A solid electrode, such as an indium tin oxide electrode, is modified by the bioprobes described herein, that are immobilized to the surface of the electrode. The bioprobe hybridize with complementary target nucleic acid sequences, and this event is detected by the reporter system As used herein, the term "electrode" means a composition which is able to carry or sense an electrical current or charge, and then convert it to a measurable signal. In some embodiments, an electrode is a solid substrate comprising a conducting material or a semiconducting material.

Electrode material can be selected according to desired redox potential range, ease of surface attachment of nucleic acid to surface, and appropriate or desired optical properties. As provided above, one limitation in the selection of an electrode material is that it cannot be identical to the material that the detection probe nanoparticle comprises. Electrode materials include, but are not limited to, certain metals and their oxides, such as gold, platinum, palladium, aluminum, indium tin oxide (ITO), tin oxide, fluorine-doped tin oxide, cadmium oxide, iridium oxide, ruthenium oxide, zinc tin oxide, antimony tin oxide, platinum oxide, titanium oxide, palladium oxide, aluminum oxide, molybdenum oxide, tungsten oxide, and others. In one particular embodiment, the electrode comprises indium tin oxide (ITO).

The electrode can comprise a single conductive material or multiple conductive materials. The conductive electrode material can be layered over a second material, such as a polymer or otherwise non-conducting surface. In some embodiments, the electrode is formed on a solid, non-conducting substrate. The substrate can comprise a wide variety of materials, including but not limited to glass, fiberglass, teflon, ceramics, silicon, mica, plastic (including acrylics, polystyrene and copolymers of styrene and other materials), polypropylene, polyethylene, polybutylene, polycarbonate, polyurethanes, TEFLON™, combinations thereof, and the like. Alternatively, a support can be constructed from a polymer material such as high density polyethylene (HDPE), often used in 96-well titer plates. In yet another example, a polyacrylamide gel can be employed as a solid support for the electrode (Dubiley et al., (1997) *Nucleic Acids Res.* 25: 2259-2265).

Solid substrates on which electrodes may be formed also include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g., all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In some embodiments, and as discussed in more detail herein, the electrode can optionally and further comprise a passivation agent. As used herein, the term "passivation" generally means the alteration of a reactive surface to a less reactive state. Passivation can refer to, for example, decreasing the chemical reactivity of a surface or to decreasing the affinity of a surface for nucleic acids. Stated differently, passivation is a method by which a surface is coated with a moiety having the ability to block subsequent binding to the surface at points where the moiety is bound.

In some embodiments, a passivation agent is in the form of a monolayer on the electrode surface. The efficiency of hybridization may increase when the detection probe is at a distance from the electrode. A passivation agent layer facilitates the maintenance of the probe away from the electrode surface. In addition, a passivation agent can serve to keep charge carriers away from the surface of the electrode. Thus, this layer can help to prevent direct physical or electrical contact between the electrodes and the nanoparticles of the detection probes, or between the electrode and charged species within the redox compound solution. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist.

In some embodiments, the electrode comprises a plurality of bioprobes attached to the electrode surface in an array format. As used herein, the terms "nucleic acid microarray," and "nucleic acid hybridization array" are used interchangeably, and mean an arrangement of a plurality of nucleobase sequences (e.g., bioprobes) bound to a support (e.g., an electrode). The terms "addressable array" and "array" are used interchangeably, and mean a plurality of entities arranged on a support in a manner such that each entity occupies a unique and identifiable position. In the methods described herein, the entities are bioprobes (e.g., capture oligonucleotides) immobilized to the surface of an electrode. As used herein, the terms "immobilize" and "attach" are used interchangeably to mean a chemical and/or mechanical association of one moiety with one or more surfaces (e.g., solid surfaces). The association can be covalent or non-covalent, and can be direct or indirect.

In some embodiments, bioprobes attached to the surface of an electrode are ordered such that each bioprobe sample has a unique, identifiable location on the support. The physical location on the electrode where a bioprobe is attached or immobilized is referred to herein as an "attachment point." The identity of a bioprobe bound to an electrode at a given location can be determined in several ways. One exemplary way to correlate a bioprobe with its location is to attach the bioprobe to the support at a known position (see, e.g., Pirrung, (1997) *Chem. Rev.* 97: 473-486). Discrete locations on the support can be identified using a grid coordinate-like system. In this approach, the working area of the support surface can be divided into discrete areas that may be referred to interchangeably as "spots" or "patches". Different bioprobes can subsequently be attached to the surface in an orderly fashion, for example, one bioprobe, or one sample of identical bioprobes, to a spot. In this strategy, the probe oligomers can be applied one or several at a time. In one exemplary method, sites at which it might be desirable to temporarily block probe binding can be blocked with a blocking agent. The blocking agent can be subsequently removed and the site freed for probe binding. This process can be repeated any number of times, thus facilitating the attachment of a known probe at a known location on a support.

Localizing bioprobes to an electrode surface at known locations can involve the use of microspotting. In this approach, the location of the bioprobes on an electrode surface is determined by the ordered application of probe samples in a group. That is, bioprobes are ordered in known locations prior to application to the electrode surface. In this way, the location of each probe is known as it is applied. Appropriate devices for carrying out this approach are commercially available and can be used with the detection methods described herein.

As set forth above, in some embodiments a singlestranded nucleic acid sequence is used as a bioprobe. For example, a bioprobe can comprise a single-stranded cDNA sequence complementary to a target gene of interest or to a target domain thereof. The bioprobe can be attached to the electrode surface indirectly via an "attachment linker," as defined herein. In this embodiment, one end of an attachment linker is attached to a bioprobe, while the other end (although, as will be appreciated by those in the art, it need not be the exact terminus for either) is attached to the electrode.

The method of attachment of the bioprobe to the attachment linker can generally be done as known in the art, and will depend on the composition of the attachment linker and the bioprobe. In general, the bioprobe is attached to the attachment linker through the use of functional groups on each moiety that can then be used for attachment. Exemplary functional groups for attachment are amino groups, carboxy groups, oxo groups and thiol groups. Using these functional groups, the bioprobes can be attached using functional groups on the electrode surface.

In one example of an attachment approach suitable for attachment of bioprobes to an electrode surface, one or more probe capture sequences are initially incubated with a solution of a thio-alcohol for a pre-selected period of time. In some embodiments, C6 mercaptohexanol is employed as a thio-alcohol. Thioalcohol and bioprobe are added in amounts so as to bring the final concentration of bioprobe in the solution to about 20% or less. The incubation time permits the covalent association of the 3' end of the bioprobe oligonucleotide with the hydroxyl group of the thio-alcohol. The solution is then exposed to the surface of a support under conditions that permit association of the sulfur atom of the thio group with the surface of the support. Suitable equipment is commercially available and can be used to assist in the binding of a target sequence to a support surface.

In another specific example, a monolayer of 12-phosphonododecanoic acid is formed on the electrode surface. The carboxylic acid of 12-phosphonododecanoic acid is then activated by 1-ethyl-3-(3-dimethylaminopropyl) carbodiimide hydrochloride (EDC) to form an O-acylisourea intermediate. See, e.g., S. H. Brewer et al., Langmuir (2002) 18, 6857-6865; B. L. Frey and R. M. Corn, *Analytical Chemistry* (1996) 68, 3187-3193; M. Burgener et al., *Bioconjugate Chemistry* (2000) 11, 749-754; K Kerman et al., *Analytica Chimica* Acta (2002) 462, 39-47; E. Huang et al., *Langmuir* (2000) 16, 3272-3280; and G. T. Hermanson, *Bioconjugate Techniques* (1996) (Academic Press: San Diego). This activated carboxylic acid group is attacked by the primary amine (acting as a nucleophile) of a 5'-modified C3H2 singlestranded DNA strand to form an amide bond between the monolayer of 12-phosphonododecanoic acid and the 5' modified C3H2 ssDNA.

Other functional groups useful for attaching oligonucleotides to solid surfaces (i.e., electrodes and nanoparticles) include, for example, moieties comprising thiols, carboxylates, hydroxyls, amines, hydrazines, esters, amides, halides, vinyl groups, vinyl carboxylates, phosphates, silicon-containing organic compounds, and their derivatives. Other functional groups useful for attachment include phosphorothioate groups (see, e.g., U.S. Pat. No. 5,472,881 for the binding of oligonucleotide-phosphorothioates to gold surfaces), aminosilanes (see, e.g., K. C. Grabar et al., *J. Am. Chem. Soc.* (1996) 118,1148), and substituted alkylsiloxanes (see, e.g. Burwell, *Chemical Technology* 4, 370-377 (1974) and Matteucci and Caruthers, *J. Am. Chem. Soc*, 103, 31853191 (1981) for binding of oligonucleotides to silica and glass surfaces, and Grabar et al., *Anal. Chem.*, 67,735-743, for binding of aminoalkylsiloxanes and for similar binding of mercaptoaklylsiloxanes). Oligonucleotides terminated with a 5' thionucleoside or a 3' thionucleoside can also be used for attaching oligonucleotides to solid electrode surfaces. The length of these attaching functional groups is chosen such that the conductivity of these molecules does not hinder electron transfer from the nanoparticle to the electrode via the hybridized probe and target nucleic acids. Stated differently, these functional groups are preferred to have higher conductivities than double-stranded nucleic acid.

In some embodiments, a "tag" or "linker" nucleic acid sequence can be employed to attach bioprobes to electrode surfaces. When a tag sequence is employed, an electrode can comprise a tag nucleic acid complement. A tag complement is a sequence that is complementary to a tag sequence associated with a bioprobe. Thus, when a bioprobe comprising a tag sequence is contacted with an electrode comprising a tag complement under suitable hybridization conditions, a duplex can form.

A tag sequence can comprise, for example, a sequence that is complementary to a support-bound tag complement. A tag sequence can be associated with a target sequence, which can then be amplified by PCR prior to association with a nanoparticle. The PCR amplicon will comprise a nucleic acid sequence comprising the tag sequence and a target target sequence. The PCR amplicon then comprises a sequence that is complementary to a support-bound tag complement. Inclusion of a tag sequence, for example as a component of a target sequence, offers the advantage that a support need not be specific for a given target sequence, but rather can be universal in the sense that it is specific for a tag complement, but not for any particular target sequence. Thus, by employing a tag complement, an electrode (or nanoparticle, as described herein) can be independent of the source of a bioprobe oligonucleotide (as to species, etc.) in the sense that the electrode can be specific for a tag sequence, but not for any particular bioprobe sequence. Thus, by employing a method comprising the use of a tag-tag complement approach, the need to form different electrode supports for different probe and/or target sequences is mitigated. See, e.g., WO 94/21820, WO 97/31256, WO 96/41011 and U.S. Pat. No. 5,503,980.

Following attachment of a bioprobe to the surface of the electrode, the areas of the electrode surface to which no probe is bound can be passivated, as defined above. A passivation process can be implemented after probes are bound to the support, and can include sequential synthesis and co-deposition approaches, as is known in the art. In some embodiments, passivation is accomplished by exposing the surface to thio-alcohol, as described above. For example, the same thio-alcohol can be used to passivate the surface as was used in attaching the probe to the surface. In some embodiments, thio-alcohols of shorter or longer length than those used to attach bioprobes can be employed.

In some embodiments, other molecules, i.e., "passivation moieties" can be used passivate the surface of a support. For example, polyethylene glycol (PEG), various alcohols and carboxylates can all be used to passivate the surface of a support, as can COO— and CONH2 moieties. In some embodiments, passivation moieties can also be non-covalently or covalently attached. Indeed, virtually any material can be used to passivate a support surface, with the understanding that the passivation material must associate with the support to form a protective layer coating the support, and that the passivating process, which can be performed after a probe is already associated with the surface of the support, does not damage any probes already bound to the support. As described above, a passivation step can also be performed to reduce the potential for nonspecific association between a nanoparticle complex and a support.

In analyzing a liquid sample using electrodes and electronic equipment and techniques, the size and spacing of electrodes can affect whether diffusion of an analyte through the sample to an electrode occurs by a planar or non-planar path. Micro-electrode arrays are of a size and spacing such that in detecting chemical species of a solution, the species will diffuse toward or approach an electrode of the micro-electrode array in a non-planar fashion, e.g., in a curved or hemispherical path of diffusion. In contrast, non-microclectrodes, i.e., "macro-electrodes," cause diffusion of an analyte through a solute according to a substantially planar path. It is also understood that some electrode configurations can cause diffusion to take place by a mix of planar and non-planar paths, in which case the electrodes can be considered a micro-electrode array, especially if the diffusion occurs predominantly (e.g., greater than 50%) according to a non-planar path, or if the size of the electrodes is less than 100 μm.

The electrodes of a micro-electrode array are positioned near each other in an arrangement that will result in non-planar diffusion as described. The arrangement of the electrodes can be any arrangement that results in such diffusion, with a working and a counter electrode being substantially evenly spaced from each other. One electrode may be arranged into a shape or figure or outline that will produce interstices within which the second electrode may be placed. For instance, one electrode can be arranged as an increasing radius, substantially circular spiral, with a continuous, long and narrow interstitial area being created between each successively larger revolution of electrode. The other electrode can be positioned in the interstitial area between revolutions, while the electrodes remain insulated from one another. The width and spacing of the electrodes can be arranged to result in micro-electrode array performance.

According to other forms of such micro-electrode arrays, the spiral may not be substantially circular, but could include linear, square, angled, or oblong or oval features. Or, the electrodes could be arranged in any other geometric form whereby the electrodes are placed adjacent to each other and within the other's respective interstitial area, e.g., by following a similar path separated by a substantially uniform gap.

In one particular embodiment, the micro-electrode can be arranged into an interdigitated array, meaning that at least a portion of electrode elements of the working electrode are placed substantially parallel to and in alternating succession with at least a portion of the electrode elements of the counter electrode, e.g., in an alternating, "finger-like" pattern. Such interdigitated micro-electrode arrays include electrode elements (sometimes referred to as "fingers") and a common element ("contact strip") which commonly connects the electrode elements.

The electrodes and their components can be of dimensions, meaning the width of the electrode components as well as the separation between components that can provide an array with useful properties, e.g., useful or advantageous capabilities with respect to contacting a substance or measuring electrical properties. Advantageously, interdigitated arrays can be prepared at dimensions that allow for contact with and measurement of electrical properties of a relatively small sample of a substance.

The thickness of the electrode components can be sufficient to support a desired electric current. Exemplary thicknesses can be in the range from about 20 to 200 nanometers (nm), with an exemplary thickness being about 10-50 nm.

The electrodes can independently have a number of interdigitated electrode elements sufficient to provide utility, e.g., allowing contact with a substance to measure its electrical behavior. Conventionally, the array can have substantially the same number (equal, plus or minus one) of electrode elements in the working electrode as are in the counter electrode, allowing the electrode elements to be paired next to each other in an alternating sequence. In some embodiments of the array, such as in some of the applications described below for electrochemical sensors, each electrode of an array may typically have from about 4 to about 30 electrode elements.

An exemplary electrode is a nanostructured microelectrode (NME). NMEs are electrodes, which are nanotextured and thus have an increased surface area. NMEs of the above-described materials are highly conductive and form strong bonds with the bioprobes. Exemplary NMEs have a height in the range of about 0.5 to about 100 microns ($\mu$m), for example in the range of about 5 to about 20 microns. (e.g., 10 microns); a diameter in the range of about 1 to about 10 microns; and have nanoscale morphology (e.g., are nanostructured on a length scale of about 1 to about 300 nanometers and more preferably in the range of about 10 to about 20 nanometers). NMEs can be any of a variety of shapes, including hemispherical, irregular (e.g., spiky), cyclical (wire-like) or fractal (e.g., dendritic). The surface of an NME may be further coated with a material, which maintains the electrode's high conductivity, but facilitates binding with a probe. For example, nitrogen containing NMEs (e.g., TiN, WN or TaN) can bind with an amine functional group of the probe. Similarly, silicon/silica chemistry as part of the NME can bind with a silane or siloxane group on the probe.

Reporter Detection Systems

Reporter systems may include chemical or biological reporters. In some embodiments, the reporter system may be an enzyme fragment, (see, e.g., US Patent Application No. 2007/0105160, incorporated by reference herein in its entirety), a protein (e.g., c-myc or other tag protein or fragment thereof), an enzyme tag, a fluorescent tag, a fluorophore tag, a chromophore tag, a Raman-activated tag, a chemiluminescent tag, a quantum dot marker, an antibody, a radioactive tag, or a combination thereof. In some aspects, enzyme activity is monitored before and after treatment to determine if enzyme activity is modulated by treatment with test compounds or agents. In other aspects, fluorescent activity is monitored before and treatment to determine if marker levels, for example, FRET-induced fluorescent levels, are modulated by treatment with test compounds or agents.

In some embodiments, the fluorescent tag includes a fluorescent dye or fluorophore. A diversity of fluorophores with a distinguishable color range allows visualization of multiple targets in parallel. Examples of fluorescent dyes developed as labels include fluorescein and rhodamine dyes (collectively called xanthene dyes). For example, fluorescein type dyes, such as FAM, JOE, HEX and NED are used for preparing real-time PCR probes, or so-called TaqMan® probes (Holland et al., *Proc. Natl. Acad. Sci. USA* 88, 7276(1991); Lee et al., *Nucleic Acids Res.* 21, 3761(1993). Likewise, various rhodamine dyes have been used for preparing real-time PCR probes based on oligonucleotides homo-doubly labeled with two identical dyes (Mao, et al., US patent application No. 20050272053). Fluorescently labeled antibodies are important tools in fluorescence immunochemistry-based detections, and fluorescein and rhodamine dyes were among the first dyes used for preparing antibody conjugates. However, many of these xanthenes dyes suffer from problems of fluorescence quenching and poor water solubility.

Xanthene dyes which absorb and emit in a variety of colors may also be used as a reporter system. Xanthene dyes with short wavelength absorption/emission include, for example, fluorescein and rhodamine 110 and sulfonated rhodamine 110. Xanthenes dyes with longer wavelength absorption/emission profile include the fluorescein derivative JOE, which has a methoxy substituent at the 4 and 5-positions, respectively, has absorption/emission maxima at 520/548 nm, compared to the parent dye fluorescein (or FAM), which has absorption/emission at 495/520 nm. The rhodamine dye ROX has absorption/emission at 575/602 nm, compared to the parent rhodamine dye carboxy-rhodamine 110, which absorbs and emits at 502/524 nm. Additional dyes are described by Sauer, et al. *Journal of Fluorescence* 5(3), 247(1995), David, et al. *Tetrahedron Letters* 49(11), 1860(2008) and Liu, et al. *Tetrahedron Letters* 44, 4355(2003).

Electrocatalytic Reporter Groups

The redox reporter can be a redox-active metal center or a redox-active organic molecule. It can be a natural organic cofactor such as NAD, NADP, FAD or a natural metal center such as Blue Copper, iron-sulfur clusters, or heme, or a synthetic center such as an organometallic compound such as a ruthenium complex, organic ligand such as a quinone, or an engineered metal center introduced into the protein or engineered organic cofactor binding site. Cofactor-binding sites can be engineered using rational design or directed evolution techniques. The redox reporter can be bound covalently or non-covalently to the protein, either by site-specific or adventitious interactions between the cofactor and protein. It can be intrinsic to the protein such as a metal center (natural or engineered) or natural organic (NAD, NADP, FAD) or organometallic cofactor (heme), or extrinsic (such as a covalently coupled synthetic organometallic cluster). The redox reporter can be, for example, linked (e.g., covalently) to a residue on the protein surface.

The redox reporter can be a metal-containing group (e.g., a transition metal-containing group) that is capable of reversibly or semi-reversibly transferring one or more electrons. A number of possible transition metal-containing reporter groups can be used. Advantageously, the reporter group has .a redox potential in the potential window below that subject to interference by molecular oxygen and has a functional group suitable for covalent coupling to the protein (e.g., thiol-reactive functionalities such as maleimides or iodoacetamide for coupling to unique cysteine residues in the protein). The metal of the reporter group should be substitutionally insert in either reduced or oxidized states (i.e., advantageously, exogenous groups do not form adventitious bonds with the reporter group). The reporter group can be capable of undergoing an amperometric or potentiometric change in response to ligand binding. In one embodiment, the reporter group is water soluble, is capable of site-specific coupling to a protein (e.g., via a thiol-reactive functional group on the reporter group that reacts with a unique cysteine in the protein), and undergoes a potentiometric response upon ligand binding. Suitable transition metals for use herein include, but are not limited to, copper (Cu), cobalt (Co), palladium (Pd), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). That is, the first series of transition metals, the platinum metals (Ru, Rh, Pd, Os, Ir and Pt), along with Fe, Re, W. Mo and Tc, may be used. Exemplary metals that do not change the number of coordination sites upon a change in oxidation state, include ruthenium, osmium, iron, platinum and palladium.

The reporter group can be present in the biosensor as a covalent conjugate with the protein or it can be a metal center that forms part of the protein matrix (for instance, a redox center such as iron-sulfur clusters, heme, Blue copper, the electrochemical properties of which are sensitive to its local environment). Alternatively, the reporter group can be present as a fusion between the protein and a metal binding domain (for instance, a small redox-active protein such as a cytochrome). Preferably, the reporter group is covalently conjugated to the protein via a maleimide functional group bound to a cysteine (thiol) on the protein. In any case, the reporter group is attached to the protein so that it is located between the protein and the electrode.

In the instant embodiment, to transduce nucleic acids hybridization into an electrical signal, an electrocatalytic reporter system previously developed by our laboratory is used (Lapierre, M. A. et al., *Anal. Chem.* 2003, 75, 6327-6333). This reporter system relies on the accumulation of $[Ru(NH_3)_6]^{3+}$ at electrode surfaces when polyanionic species like nucleic acids bind, and the catalysis of the reduction of Ru(III) via the inclusion of $[Fe(CN)_6]^{3-}$, which regenerates Ru(III) and allows multiple reductions per metal center. When PNA-modified NMEs were challenged with a complementary sequence, detectable signal changes could be clearly detected through the femtomolar concentration range. Negligible signal changes were observed with completely non-complementary sequences.

Nucleic Acid Targets

A target sequence can be selected on the basis of the context in which the present methods are employed. Target sequences can vary widely. For example, desirable target sequences include, but are not limited, to characteristic or unique nucleic acid sequences found in various microbes or mutated DNA that can be used in the diagnosis of diseases, in environmental bioremediation, in the determination of genetic disorders, and in genetic epidemiology.
Functional equivalents of known sequences can also be used as target sequences.

The target sequence may be a portion of a gene, a regulatory sequence, genomic DNA, cDNA, RNA including mRNA and rRNA, or others. The target sequence can be a target sequence from a biological sample, as discussed herein, or can be a secondary target such as a product of an amplification reaction. The target sequence can take many forms. For example, a target may be contained within a larger nucleic acid sequence, i.e., all or part of a gene or mRNA, a restriction fragment of a plasmid or genomic DNA, among others. Target nucleic acids can be excised from a larger nucleic acid sample using restriction endonucleases, which sever nucleic acid sequences at known points in a nucleic acid sequence. Excised nucleic acid sequences can be isolated and purified by employing standard techniques. Target sequences can also be prepared by reverse transcription processes. See, e.g., Sambrook et al., Molecular Cloning: A Laboratory Manual (Cold Spring Harbor, N.Y. (1992)). A target sequence can comprise one or more different target domains. A target domain is a contiguous, partial sequence (i.e., a sub-sequence) of the entire target sequence, and may be any nucleotide length that is shorter than the entire target sequence. In some embodiments, a first target domain of a target sequence hybridizes a capture probe, while a second and different target domain hybridizes an oligonucleotide component of a detection probe. Target domains may be adjacent or separated, as indicated. For example, a first target domain can be directly adjacent (i.e., contiguous) to a second target domain, or the first and second target domains may be separated by an intervening target domain. Assuming a 5' to 3' orientation of a target sequence, a first target domain may be located either 5' to a second target domain, or 3' to a second domain.

If desired, a target sequence may further comprise an additional moiety such as one partner of a ligand-binding pair, in order to facilitate binding to a detection probe comprising a nanoparticle attached to the other partner of the ligand-binding pair. For example, the target sequence may comprise a biotin moiety, which will facilitate binding to a detection probe comprising a nanoparticle attached to streptavidin. The biotin moiety may be incorporated into the target sequence using amplification methods that are analogous to known methods used to incorporate fluorescent moieties into target molecules, as set forth in more detail below. Nucleic acid sequences of any practical length can be used as a target sequence. Generally, a target sequence is between 10 and 50 nucleotides in length, and thus target sequences of 10, 15, 20, 25, 30, 35, 40, 45 or more nucleotides can be employed. However, target sequences of any length can be employed in the methods disclosed herein, and in some cases, may be shorter than ten nucleotides and longer than 50 nucleotides. For example, target sequences may be about 60 nucleotides long, about 75 nucleotides long, about 85 nucleotides long, about 100 nucleotides long, about 200 nucleotides long, about 300 nucleotides long, about 400 nucleotides long, about 500 nucleotides long, or even longer. In some instances, the target sequence may be between 60-500 nucleotides long. If desired by the artisan, a target sequence may be fragmented prior to hybridization steps by using enzymatic, mechanical or other means as known in the art.

In some embodiments, target sequences can be isolated from biological samples, including, but not limited to, bodily fluids (e.g., blood, urine, serum, lymph, saliva, anal and vaginal secretions, perspiration semen, etc., of virtually any organism); environmental samples (e.g., air, plant, agricultural, water and soil samples); and research samples (i.e. amplification reaction products, purified samples such as purified genomic nucleic acids, and unpurified samples of bacteria, virus, genomic DNA, etc.).

If required, the target nucleic acid can be isolated from source biological samples using known techniques. For example, samples can be collected and concentrated or lysed, as required. Appropriate adjustment of pH, treatment time, lytic conditions and sample modifying reagents can also be made in order to optimize reaction conditions. Such modification techniques are well known to those of skill in the art. Methods for nucleic acid isolation and purification can comprise simultaneous isolation of, for example, total nucleic acid, or separate and/or sequential isolation of individual nucleic acid types (e.g., genomic DNA, cDNA, organelle DNA, genomic RNA, mRNA, polyA+RNA, rRNA, tRNA) followed by optional combination of multiple nucleic acid types into a single sample.

Methods for nucleic acid isolation can optionally be optimized to promote recovery of pathogen-specific nucleic acids. In some organisms, for example fungi, protozoa, grampositive bacteria, and acid-fast bacteria, cell lysis and nucleic acid release can be difficult to achieve using general procedures, and therefore a method can be chosen that creates minimal loss of the pathogen subset of the sample. Semi-automated and automated extraction methods can also be used for nucleic acid isolation.

In some embodiments, a target nucleic acid comprises a double-stranded nucleic acid. Double stranded nucleic acid sequences can be prepared, for example, by isolating a double stranded segment of DNA. Alternatively, multiple copies of single stranded complementary oligonucleotides can be synthesized and annealed to one other under appropriate conditions. In order to provide a singlestranded target for hybridization, double-stranded nucleic acids are preferably denatured before hybridization. The term "denaturing" refers to the process by which strands of oligonucleotide duplexes are no longer base-paired by hydrogen bonding and are separated into single-stranded molecules. Methods of denaturation are well known to those skilled in the art, and include thermal and alkaline denaturation. RNA isolation methods are known to one of skill in the art. See, Albert et al. (1992) *J Virol* 66:5627-2630; Busch et al. (1992) *Transfusion* 32:420-425; Hamel et al. (1995) *J Clin Microbiol* 33:287-291; Herrewegh et al. (1995) *J Clin Microbiol* 33:684-689; Izraeli et al. (1991) *Nuc Acids Res* 19:6051; McCaustland et al. (1991) *J Virol Methods* 35:331342; Nataraian et al. (1994) *PCR Methods Appl* 3:346-350; Rupp et al. (1988) *BioTechniques* 6:56-60; Tanaka et al. (1994)*J Gen Virol* 75:2691-2698; and Vankerckhoven et al. (1994) *J Clin Microbiol* 30:750-753.

Targeting mRNA is attractive given that most mRNAs exist as linear sequences and therefore denaturation is not required. Multiple copies of mRNAs are typically present within a cell, providing built-in amplification at the cellular level, improving the prospects for the direct analysis of small numbers of cells. However, the large sizes of mRNAs present a challenge for chipbased sensing as the slow diffusion of such large molecules can impede rapid analysis.

To aid in the detection of large molecules, we have increased the reach of the sensor into the solution volume, thus providing greater interaction between the target molecules in solution and the bio-probe molecules tethered to the sensor surface. Using existing diffusional models, (P. E. Sheehan et al., *Nano Lett.* 2005, 5, 803; and P. R. Nair, et al., *Nano Lett.* 2008, 8, 1281) and taking into consideration the copy number of the target mRNA and its rate of diffusion, when the spatial footprint of our sensors is increased to—100 microns, we can detect as few as 10 cells expressing the target mRNA within analysis times approaching 30 minutes (a volume of 30 microliters was used in this calculation to yield a concentration of 1.7 fM for the mRNA)

In some embodiments, an increase of about 10% to about 20% in signal, of about 10% to about 40% in signal, or of about 1% to about 20% in signal as compared to a control signal in the absence of target nucleotide, is obtained when the bioprobe hybridizes to a target nucleotide. In certain other embodiments, the increase is about 30%. In certain embodiments, the increase in signal is about 40% when the bioprobe is hybridized to a target nucleotide. In some embodiments the increase is about 50% to about 60%. In certain embodiments, the increase in signal is about 70%, about 80%, about 90%, about 100%, about 125%, about 150%, about 175%, or about 200% when the target nucleic acid is hybridized to the bioprobes disclosed herein.

In some embodiments, a decrease of about 10% to about 20% in signal is obtained when the bioprobe hybridizes to a target nucleotide. In certain other embodiments, the decrease is about 30%. In certain embodiments, the decrease in signal is about 40% when the bioprobe is hybridized to a target nucleotide. In some embodiments the decrease is about 50% to about 60%. In certain embodiments, the decrease in signal is about 70%, about 80%, about 90%, about 100%, about 125%, about 150%, about 175%, or about 200% when the target nucleic acid is hybridized to the bioprobes disclosed herein.

The following examples are included for illustrative purposes only and are not intended to limit the scope of the embodiments. The specific methods exemplified can be practiced with other species. The examples are intended to exemplify generic processes.

EXAMPLES

Example 1

General Design Strategy for Bioprobe

Herein, bioprobe molecules are disclosed that exhibit improved water solubility and monolayer-forming properties with substantially no or little aggregation detected that can appreciably interfere with binding of the disclosed bioprobe molecules with a target nucleic acid sequence. Introduction of charged functional groups at the termini of the nucleobase sequence can beneficially alter the probe's properties, including solubility profiles. One exemplary embodiment is the attachment of charged amino acids to PNA, DNA and RNA using similar coupling chemistry to that used in traditional PNA synthesis. For example, the inclusion of sufficient charged amino acid units may improve the behaviour of the nucleobase comprising bioprobe in that solubility may be improved in aqueous solution, and may exhibit better performance when used to detect the target biomolecule of interest. In case of persistent solubility or aggregation issues, a multitude of charged amino acids may be used. The amino acids may be placed at the termini as shown in Table 3 below.

TABLE 3

Sample Bioprobe sequences

| Probe No | Sequence | SEQ ID NO |
|---|---|---|
| 1 | Cys-Gly-NB-Xaa | 1 & 16 |
| 2 | Cys-Gly-Xaa-NB-Xaa | 2 & 16 |
| 3 | Cys-Gly-Xaa-Xaa-NB | 3 |
| 4 | Cys-Gly-Xaa-Xaa-Xaa-NB-Xaa | 4 & 16 |
| 5 | Cys-Gly-Xaa-Xaa-Xaa-NB-Xaa-Xaa | 5 & 17 |
| 6 | Cys-Gly-Xaa-Xaa-Xaa-NB-Xaa-Xaa-Xaa | 6 & 18 |

TABLE 3-continued

Sample Bioprobe sequences

Figure 2D:
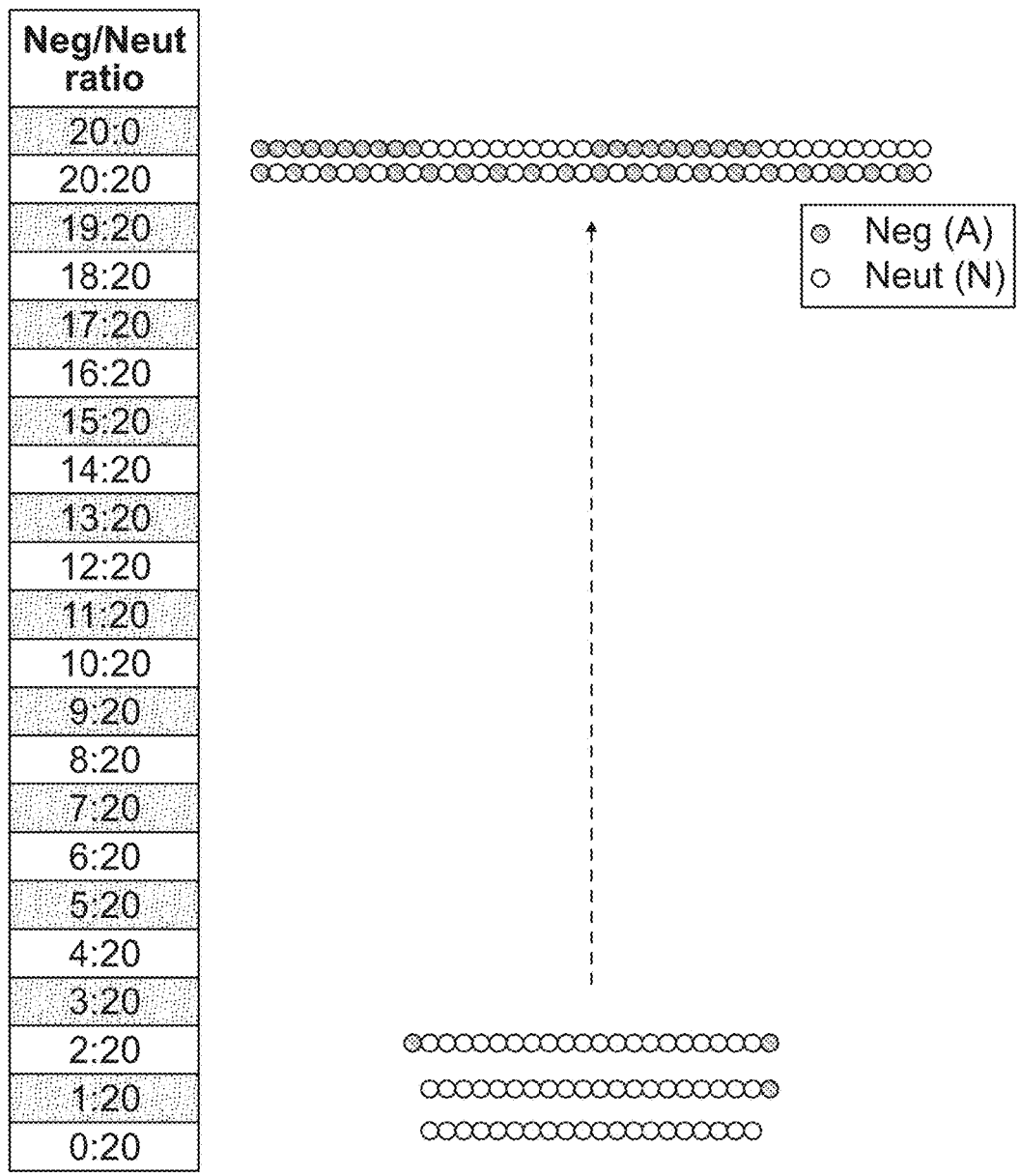

| Probe No | Sequence | SEQ ID NO |
|---|---|---|
| 7 | Cys-Gly-Xaa-NB-Xaa-NB | 7 & 16 |
| 8 | Cys-Gly-Xaa-NB-Xaa-NB-Xaa-NB- | 8 & 16 & 16 |
| 9 | Cys-Gly-Xaa-NB-Xaa-Xaa-NB-Xaa- | 9 & 17 & 16 |
| 10 | Cys-Gly-Xaa-Xaa-NB-Xaa-NB-Xaa-Xaa | 10 & 16 & 17 | wherein Xaa is a charged amino acid such as Asp, Glu, Aad, Lys, Orn, Dab, Dap, Arg or an amino acid selected from Table 2 and NB is an oligonucleobase sequence such as a DNA, PNA or RNA. The charged amino acids may be replaced with the charged functional groups disclosed herein, including anionic functional groups such as carboxylate, sulfate or sulfonate, and cationic functional groups such as amine or guanadinum. In some embodiments, the charged functional groups are placed intermittently through the nucleobase sequence without adversely affecting the ability of the nucleobase sequence to hybridize with the target. FIG. 2D shows different strategies for placement of charged amino acids in conjugation with a 20 nucleobase bioprobe sequence.

Example 2

Target Gene bcr-abl gene fusion is specific to chronic myleoid leukemia (CML) as an interesting model system to hone the capabilities of our chip-based sensors so that small numbers of cancer cells could be analyzed. The bcr-abl mRNA transcript is a RNA molecule that is 8500 nucleotides long (F. vanRhee, et al., *Blood* 1996, 87, 5213-5217).

As described supra, using existing diffusional models, and taking into consideration the copy number of the bcr-abl fusion mRNA (~3000 copies per cell) (M. Wilda, et al., *Oncogene* 2002, 21, 5716) and its rate of diffusion, it was determined that increasing spatial footprint of our sensors to ~100 microns, would result in detection of as few as 10 CML cells within analysis times approaching 30 minutes (a volume of 30 microliters was used in this calculation to yield a concentration of 1.7 fM for the mRNA).

Example 3

Biosensor Design

Figure 1B:
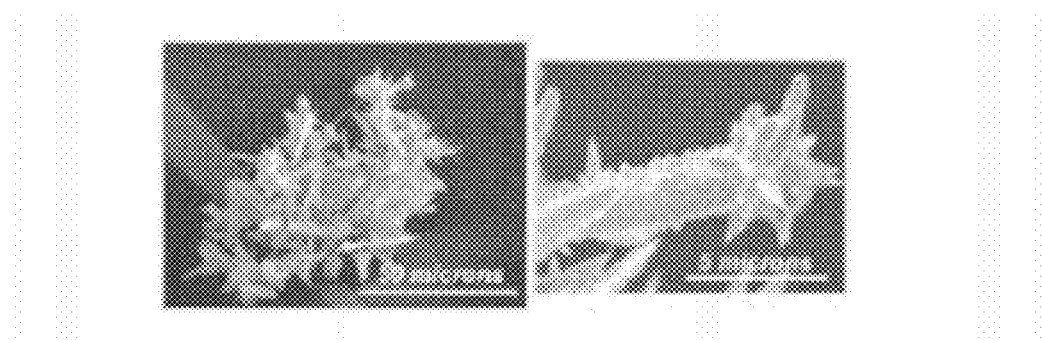
Figure 1C:
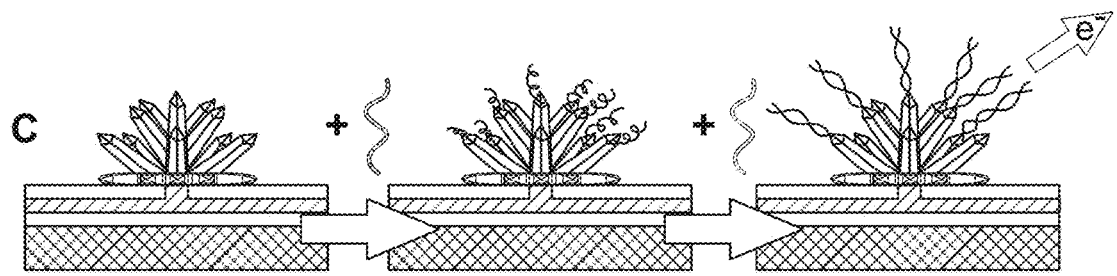
Figure 1D:
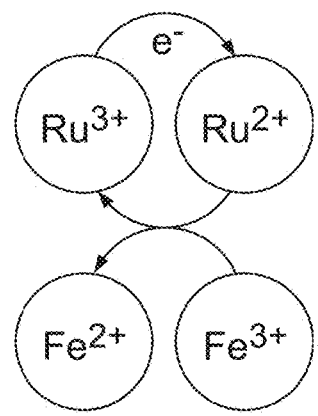
Figure 1E:
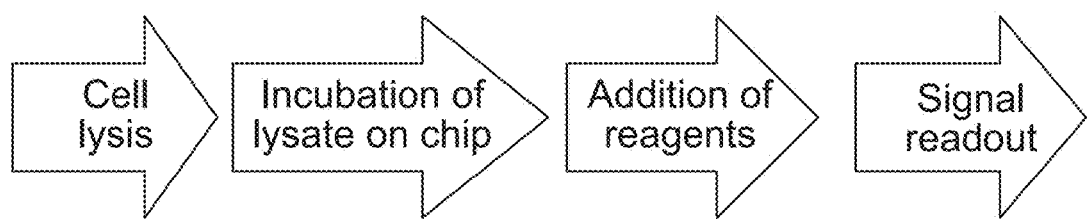
Figure 5:
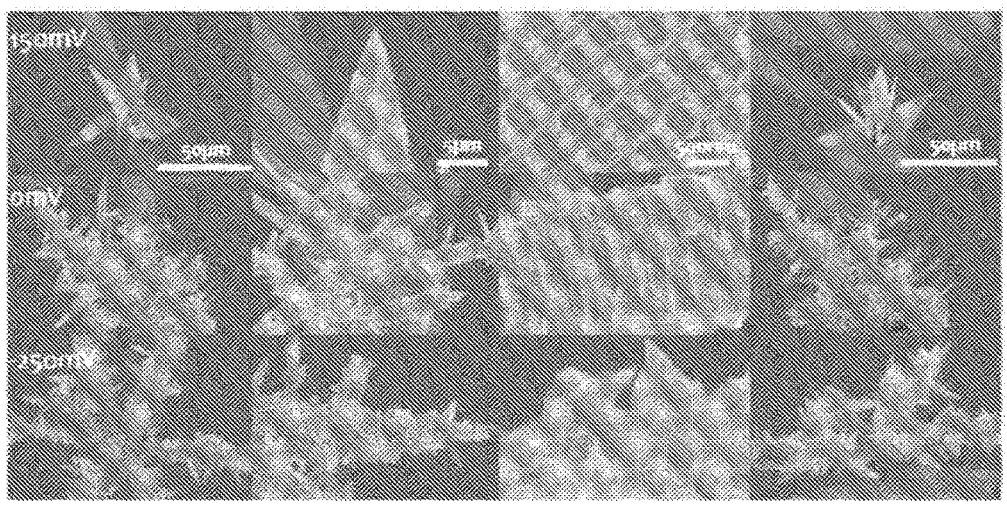
FIG. 5 shows optimization of biosensor deposition conditions: variation of electroplating potential to increase sensor footprint. 0 mV was identified as the optimal potential to use in order to generate 100 micron sensors.
Figure 6:
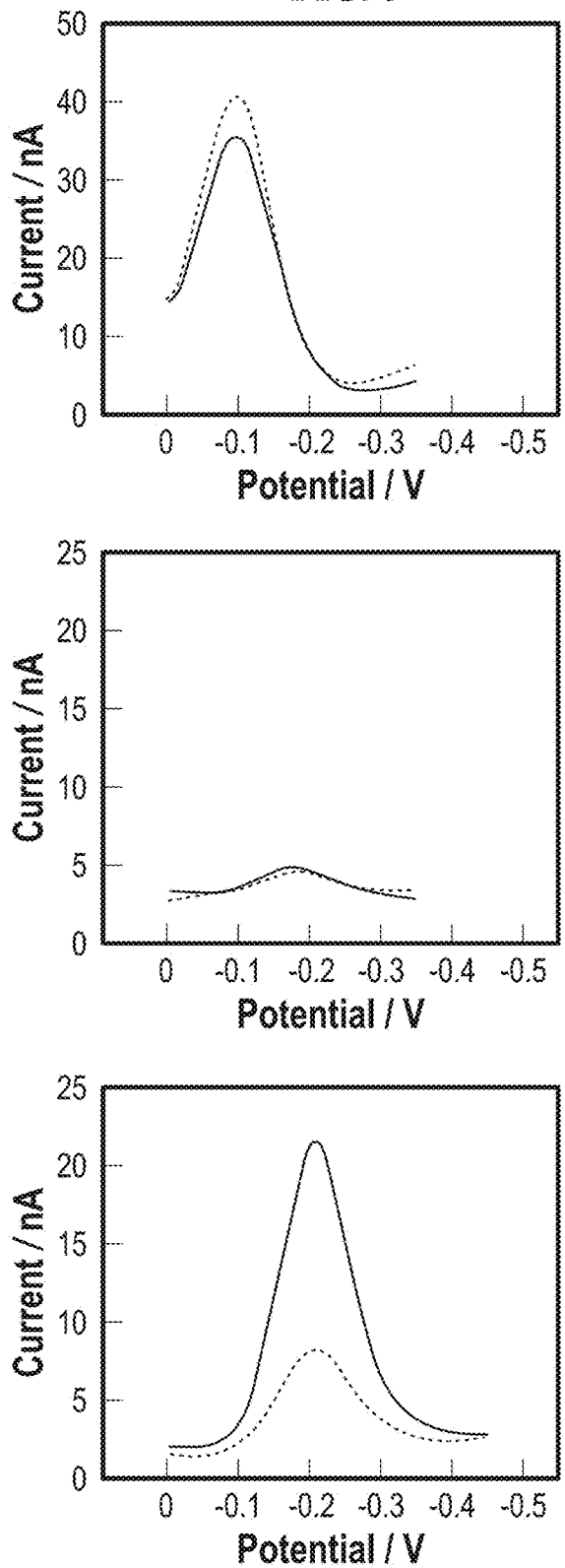
FIG. 6 shows representative differential pulse voltammograms obtained with three 25 different probe types before (dotted) and after (solid) solution of K562 mRNA with a concentration of 1 ng/ul.

Previous work on chip-based microsensors focused on palladium sensors that were 5-10 microns in diameter (L. Soleymani, et al., *Nat. Nanotechnol.* 2009, 4, 844). To extend the reach of these sensors into solution, it was necessary to use gold as the electrode material. Electroplated palladium did not produce grain sizes that allowed growth of the sensor into solution, and instead the sensors grew along the surface of the chip. In contrast, the electroplating of gold produced spiky structures with large substructures extending many microns into solution when low plating potentials were used (FIG. 5). After extensive variation of plating conditions (including plating potential, supporting electrolyte, and plating time), biosensors with the desired 100 micron footprint were obtained (FIG. 1B).

In order to test these biosensors against the bcr-abl mRNA target, bioprobes that would specifically bind to the junction region between the two fused genes were required. Initial efforts to produce a functional probe for this region (FIG. 2) included the synthesis of DNA and PNA bioprobes. When challenged with mRNA from the K562 cell line, which contains the most common form of the bcr-abl gene fusion, hybridization was not detected with either DNA bioprobe or PNA bioprobe. Hybridization analysis was carried out by monitoring reductive currents in a solution containing a Ru(III)/Fe(III) electrocatalytic reporter system. The solution used in these trials contained 1 ng/μl of total mRNA, which contained >10,000,000 copies of the target per microliter, or >20 pM—a concentration that should have been readily detectable based on our calculations. The DNA bioprobe modified biosensors exhibited high background signals and small decreases in current upon introduction of the mRNA solution. The PNA-modified biosensor exhibited a much lower background current, but here too, only small decreases in current were observed upon hybridization with mRNA rather than the expected increase.

Example 4

Bioprobe Design

Since the PNA and DNA based bioprobes failed in functioning as desired, developed herein are a new class of probe molecules: amino acid/nucleic acid chimeras (ANAs) that were necessary in order to detect a specific cancer biomarker. ANAs overcome three fundamental limitations that we found arise when using neutral probe molecules: poor solubility, aggregation, and poor monolayer quality. The resulting sensor system reported herein displays excellent sensitivity and specificity. Remarkably, it achieves this excellent performance, requiring a single, simple cell lysis step prior to analysis, even when analyzing unpurified samples.

The introduction of charged amino acids at the termini of the PNA sequence described supra beneficially altered the PNA probe's properties. Attachment of amino acids to PNAs was achieved using identical coupling chemistry to that used in traditional PNA synthesis.

The inclusion of 2 aspartic acid units—rectified the behaviour of our probe in that it was now highly soluble in aqueous solution, and exhibited much better performance when used to detect the bcr-abl mRNA. Low background currents were observed at probe-modified sensors, and significant increases occurred upon hybridization of K562 mRNA containing the fusion (FIG. 2C).

Example 5

Experimental Materials and Methods

Chemicals and materials. Gold (III) chloride (99.9%), hexaammineruthenium (III) chloride, potassium ferricyanide, magnesium chloride, and 6-mercapto-1-hexanol (97%), 10×TBE buffer, UltraPure™ Agarose, dimethylformamide, piperidine, TFA, m-cresol, TIPS, diethyl ether, acetonitrile, DTT were purchased from Sigma-Aldrich Canada Ltd.; 70% perchloric acid, sulfuric acid, ACS-grade acetone, and isopropyl alcohol were obtained from EMD; 6N hydrochloric acid was purchased from VWR. PNA monomers were purchased from Link technologies, Knorr resin was purchased from NovaBiochem; HATU and N-methylmorpholine were purchased from Protein Technologies, Inc., and RedSafe™ from FroggaBio; K562 cell line was obtained from the ATCC, 25-mL suspension flasks were purchased from Sarstedt, Iscove's Modified Dulbecco culture medium and fetal bovine serum were obtained from Invitrogen; CML patient samples were provided by Dr. Minden of Princess Margaret Hospital, whole blood was obtained at the Princess Margaret Hospital blood laboratory.

Preparation and purification of oligonucleotides. ANA and PNA oligonucleotides were synthesized using the solid-phase synthesis approach on a Prelude automated peptide synthesizer (Protein Technologies, Inc.). ANA probe corresponding to el3a2: $NH_2$-Cys-Gly-Asp-TGAAGGGCTTCT-TCCTTATT-Asp-CONH2 (SEQ ID NO: 11) and ANA probe corresponding to el4a2: $NH_2$-Cys-Gly-Asp-TGAAGGGCTTTTGAACTCTG-Asp-$CONH_2$ (SEQ ID NO: 12). PNA probes contained the same sequence but lacked the Asp residues. DNA probe was commercially purchased and a thiol containing linker was added in-house: TGAAGGGCTTTTGAACTCTG-linker-SH (SEQ ID NO: 13). Negative control probe was: $NH_2$-Cys-Gly-Asp-ATCT-GCTCTGTGGTGTAGTT-Asp-$CONH_2$ (SEQ ID NO: 14). All probe molecules were stringently purified using an Agilent 1100 series HPLC. Concentration was determined by measuring absorbance at 260 nm.

Chip fabrication. The chips were produced at the Canadian Photonics Fabrication Center. Silicon wafers were passivated using a thick layer of thermally grown 2 micron silicon dioxide. A 350-nm gold layer was deposited on the chip using electron-beam-assisted gold evaporation. The gold film was patterned using standard photolithography and a lift-off process. Using chemical vapour deposition a 500-nm layer of insulating silicon dioxide was deposited. Five (5) micron circular apertures and 2×2 mm bond pads were exposed on the electrodes through the top layer using standard photolithography.

Fabrication of microelectrodes. The chips were washed in acetone, rinsed with isopropyl alcohol and then deionized water and briefly dried with a flow of nitrogen. All electrodeposition was performed at room temperature with a Bioanalytical Systems Epsilon potentiostat with a three-electrode system containing an Ag/AgCl reference electrode and a platinum wire auxiliary electrode. The 5 micron apertures on the chips were used as the working electrode and were contacted using the exposed bond pads. Electrodeposition of gold microelectrodes were accomplished by dipping the chip into the plating solution (20 mM $H_2AuC_{14}$ in 0.5M hydrochloric acid) and applying constant of 0 mV for 175 seconds.

Modification of microelectrodes. A solution containing 5 µM thiolated PNA probe in 50 mM sodium chloride was added to the sensors and left in a dark humidity chamber overnight at room temperature for self-assembly of a monolayer. A solution of 10 µM MCH was then added to each chip for 1 hour at room temperature to block the bare surface of the NME. The chip was then washed twice with 50 mM NaCl.

Electrochemical measurements. Electrochemical signals were measured in a solution containing 10 µM $[Ru(NH_3)_6]^{3+}$ and 2 mM $[Fe(CN)_6]^{3-}$ in 1×PBS. Differential pulse voltammetry signals before and after hybridization were collected with a scan rate of 100 mV s-1 and scanned from 0 mV to −350 mV. Results were quantified by subtracting peak currents in DPV scans as follows, ΔI=Iafter hybridization-Ibefore hybridization.

Cell culture. K562 cells were cultured in 25 mL suspension cell flasks with vent caps in Iscove's Modified Dulbecco's Medium/10% fetal bovine serum. The cells were grown in a humidified incubator (70-95%) at 37.0° C. with $CO_2$ (5%). Cultures were maintained by the replacement by fresh medium every 2 to 3 days. Subculture was performed when the cell population reached 500,000 cells/mL. K562 cells and patient samples preparation. K562 cells were collected and centrifuged at 600 ref for 5 minutes at 4° C. The media was then removed and the cells were washed with equal volume of 1×PBS. The cell pellet was then resuspended in 1×PBS and used for lysis. CML patient samples frozen stock were thawed quickly at 37° C. in a water bath. Immediately, the cells were added to 10 mL of fresh media supplemented with 10% FBS and centrifuged at 400 ref for 5 minutes at 4° C. The pellet was washed fresh media and the pellet was resuspended in 1×PBS for further use. Primary samples were collected following informed consent according to an REB approved protocol.

mRNA isolation. Total mRNA was isolated from cells using Dynabeads® (Invitrogen). Quality of the mRNA sample was tested using 1% agarose gel electrophoresis.

Cell lysis. Cells lysis (K562, patient samples, whole blood) was achieved using an electrical lysis chamber. Pt wires used to produce the electric field were inserted into PDMS (polydimethylsiloxane) membrane. The channels for the cell solution to flow through were made with dull end needle and were vented with $N_2$ for 1 hour prior to use. Resuspended cells were taken into a 5 mL syringe and loaded into a syringe pump. In case of whole blood, it was diluted 100 times in IX PBS and 1 mL was loaded into a 5 mL syringe. Lysis was achieved at a flow rate 25 µL/min, 400 V and 1 mA current.

Hybridization protocol. Hybridization solutions contained either total mRNA, or unpurified cell lysate in 50 mM NaCl. Electrodes were incubated with the target sequences at 37° C. in a humidity chamber in the dark for 30 minutes and were washed extensively twice with 50 mM NaCl prior to electrochemical analysis. Hybridization volume was typically 30 µL.

Example 6

Biosensor Use in CML Detection

Figure 3:
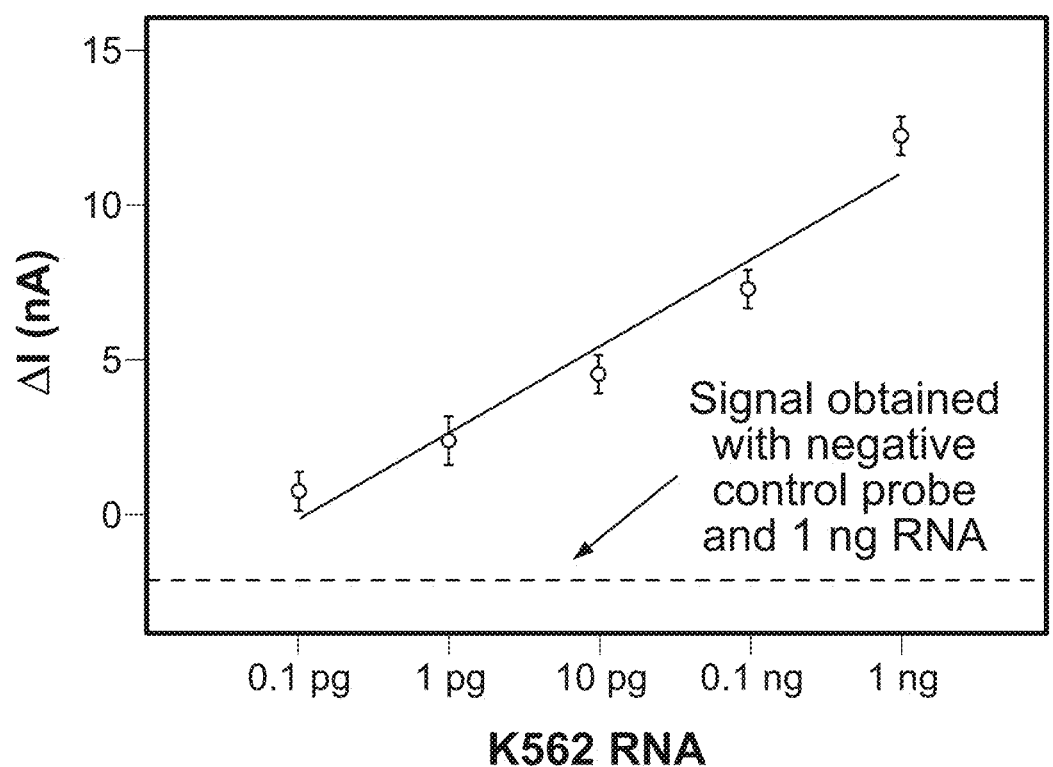
FIG. 3 shows Sensitivity of biosensors modified with an ANA bioprobe towards the mRNA from the K.562 cell line which carries the bcr-abl gene fusion.

With optimized biosensors and chimeric amino acid/nucleic acid (ANA) probes in hand, the limit of detection and dynamic range was determined when the system was challenged with purified cellular mRNA. A control probe with an unrelated sequence was monitored alongside the bcr-abl probe and showed no signal change even at the highest concentration tested, indicating that the assay had excellent specificity. Detectable signal was observed as low as 1 pg/µL of total mRNA (FIG. 3) and the signal increased linearly over four logs of target concentration. This result is comparable with a commercially available polymerase chain reaction (PCR) assay designed to specifically detect CML; the assay has a similar detection limit (Z. Jobbagy, et al., *Mol. Diagnostics,* 2007, 9, 220). This chip-based system is the first ever to exhibit PCR-like sensitivity.

While PCR is a highly sensitive technique for sequence detection, it often requires extensive sample processing and nucleic acid purification to eliminate interferents that inhibitors of the enzymes used for amplification. Given that our detection system does not rely on any enzymatic reactions, it is much more tolerant of unpurified samples.

Figures 4A, 4B, 4C, 4D, 4E:
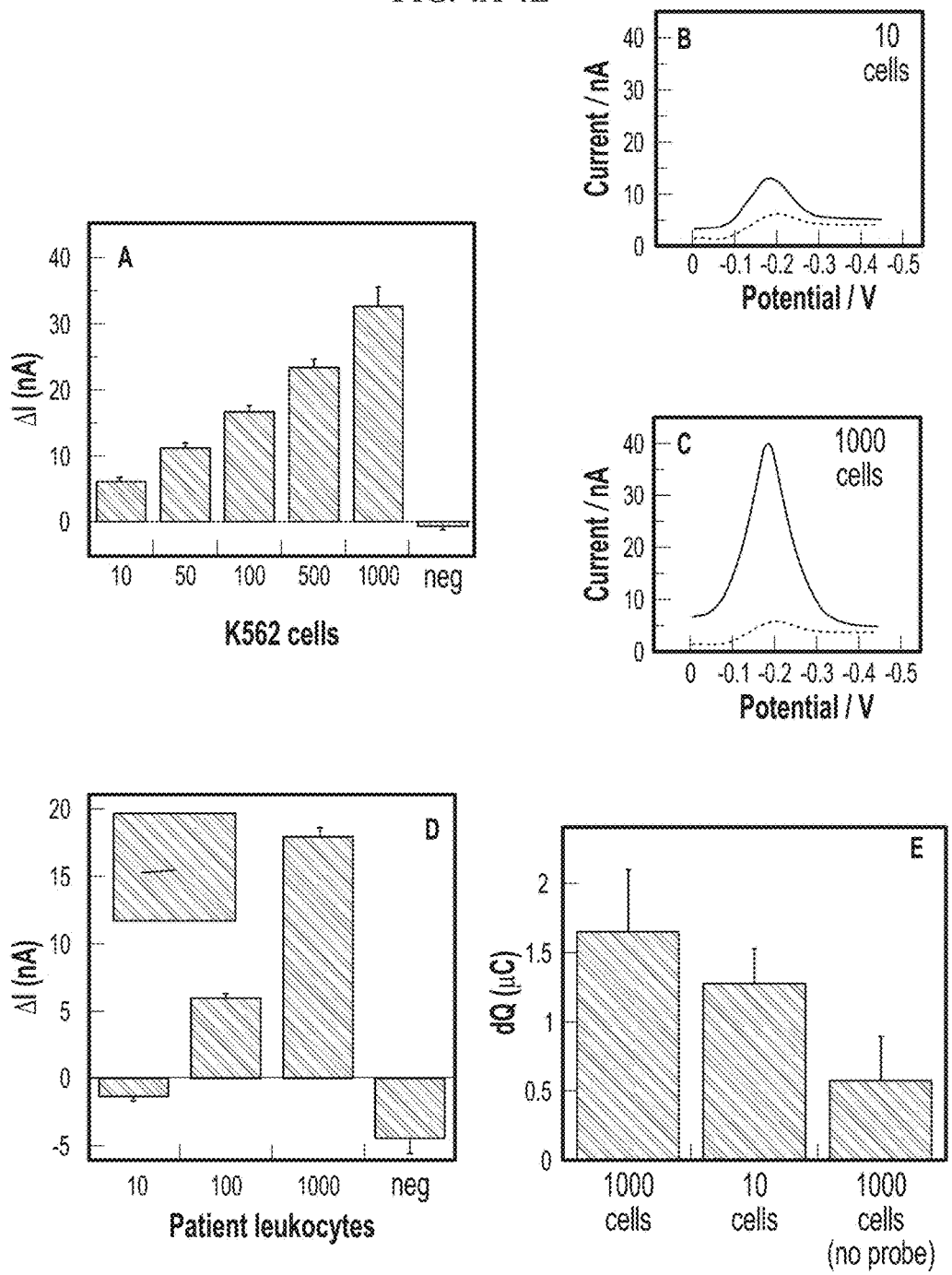
FIGS. 4A-4E depict performance of ANA-modified sensors when challenged with crude cell lysates.

To prove detection fusion mRNA from an unpurified sample, K562 cells were lysed using an electric field. Rapid lysis was achieved (under 5 minutes) without the use of added reagents. Lysates were generated containing 10 to 1000 cells; the results of their incubation with bcr-abl probe-modified sensors are illustrated in FIG. 4A. The negative control was a half-complementary probe (a probe for the el3a2 gene fusion) and was found to show no signal increase, confirming the specificity of the assay. The detection of 10 cells—present as an unpurified lysate—indicates that these biosensors are highly sensitive and robust. Leukocytes from CML patients were then analysed using the same lysis-only sample preparation procedure and the sensor and assay described above. The negative control was a probe only half complementary to the bcr-abl gene fusion. Absence of a positive signal with the negative control again confirmed the specificity of hybridization. Here the detection limit approached 100 cells, owing to the fact that the sample contained both CML cells and normal leukocytes.

Example 7

CML Detection in Blood Samples

CML samples in whole blood were analysed. Analysis of complex samples is challenging due to their heterogeneity: in particular, direct analysis in blood may be impeded by rapid degradation of nucleic acids by nucleases, and by the fouling of surfaces by the components of blood. Blood spiked with CML cells was used to determine whether the analysis of whole blood samples would be feasible. An offset of the background signal was observed when blood only was used. The use of a control probe was introduced to follow this shift, which remained constant when samples with varying numbers of K562 cells were analyzed. By referencing measurements for the target-probe case to the control-probe case, as few as 10 K562 cells were detected even in the presence of a 5,000,000-fold excess of blood cells (FIG. 3E).

This study represents the first report of highly sensitive, specific bioprobe for analysis of nucleic acid biomarkers in relevant samples. It relies on direct lysis of the cells under study within a medium—blood—that comprises a huge excess of noncomplementary molecules. Specifically, the biosensors described herein achieved detection of mRNA derived from 10 cells present as an unpurified, unprocessed lysate.

Various publications are cited herein, the disclosures of which are incorporated by reference in their entireties.

What is claimed is:

1. A bio-probe, comprising:
a nucleobase sequence capable of hybridizing to a target biomarker; at least two charged functional groups disposed intermittently through the bio-probe, wherein said charged functional groups comprise a cationic functional group, an anionic functional group, a charged amino acid, or a combination thereof; and
wherein the charged functional group inhibits aggregation of nucleobase sequences of a plurality of bio-probes.

2. The bio-probe of claim 1, wherein the nucleobase sequence is a DNA, RNA, or PNA.

3. The bio-probe of claim 1, comprising between about 10 and about 40 nucleobases.

4. The bio-probe of claim 3, wherein at least one of the nucleobases is a modified nucleobase.

5. The bio-probe of claim 1, comprising between about 1 and about 20 charged functional groups.

6. The bio-probe of claim 1, wherein said anionic functional group is a carboxylate, a sulfate, or a sulfonate.

7. The bio-probe of claim 1, wherein said cationic functional group is an amine or a guanadinum.

8. The bio-probe of claim 1 is immobilized onto a microelectrode.

9. The bio-probe of claim 8, wherein the electrode is a nanostructured microelectrode.

10. The bio-probe of claim 1, further comprising a redox reporter.

11. A method of detecting a target biomarker in a sample, comprising:
contacting the sample with a bio-probe comprising a nucleobase sequence capable of hybridizing to a target biomarker, at least two charged functional groups disposed intermittently through the bio-probe, wherein said charged functional group comprises a cationic functional group, an anionic functional group, a charged amino acid, or a combination thereof, and wherein the charged functional group inhibits aggregation of nucleobase sequences of a plurality of bio-probes;
hybridizing the bio-probe to the target biomarker; and
detecting the hybridization as being indicative of the presence of the target biomarker in the sample.

12. The method of claim 11, wherein a plurality of the bio-probes are immobilized onto distinct locations on a microelectrode.

13. The method of claim 11, wherein the detection is performed by means of a redox reporter.

14. The method of claim 11, wherein the detection is performed by observing a reporter signal, and wherein a change in reporter signal on hybridization of the bio-probe with the target biomarker, as compared to the reporter signal in the absence of hybridization of the bio-probe, is indicative of presence of the target biomarker in the sample.

15. The method of claim 11, wherein the sample is a biological fluid from an individual.

16. A biosensor, comprising:
an electrode; and
a bio-probe comprising a nucleobase sequence capable of hybridizing to a target biomarker, and at least two charged functional groups disposed intermittently through the bio-probe, wherein said charged functional group comprises a cationic functional group, an anionic functional group, a charged amino acid, or a combination thereof; and
wherein the charged functional group inhibits aggregation of nucleobase sequences of a plurality of bio-probes.

17. The biosensor of claim 16, wherein the electrode is a nanostructured microelectrode.

* * * * *